US012377238B1

(12) United States Patent
Ruppell, III et al.

(10) Patent No.: US 12,377,238 B1
(45) Date of Patent: Aug. 5, 2025

(54) AUTOMATED VENTILATOR

(71) Applicant: CORVENT MEDICAL, INC., Fargo, ND (US)

(72) Inventors: Edward F. Ruppell, III, Fargo, ND (US); John J. O'Mahony, Fargo, ND (US)

(73) Assignee: CORVENT MEDICAL, INC., Fargo, ND (US)

( * ) Notice: Subject to any disclaimer, the term of this patent is extended or adjusted under 35 U.S.C. 154(b) by 0 days.

(21) Appl. No.: 18/810,206

(22) Filed: Aug. 20, 2024

Related U.S. Application Data

(63) Continuation of application No. 18/254,353, filed as application No. PCT/US2021/062300 on Dec. 8, 2021.

(Continued)

(51) Int. Cl.
*A61M 16/12* (2006.01)
*A61M 16/00* (2006.01)
(Continued)

(52) U.S. Cl.
CPC ........ *A61M 16/12* (2013.01); *A61M 16/0057* (2013.01); *A61M 16/0066* (2013.01);
(Continued)

(58) Field of Classification Search
CPC .......... A61M 16/0057; A61M 16/0063; A61M 16/0066; A61M 16/024; A61M 16/0883;
(Continued)

(56) References Cited

U.S. PATENT DOCUMENTS 5,299,568 A * 4/1994 Forare ................. A61M 16/202
128/205.24
6,076,523 A  6/2000 Jones et al.
(Continued)

FOREIGN PATENT DOCUMENTS

| WO | WO-0045883 A1 * | 8/2000 | ........ A61M 16/0069 |
| WO | 2019/189126 A1 | 10/2019 | |
| WO | 2020/081394 A1 | 4/2020 | |

OTHER PUBLICATIONS

International Search Report for PCT/US2021/062300, mailed Apr. 1, 2022, 5 pages.

(Continued)

*Primary Examiner* — Joseph D. Boecker
(74) *Attorney, Agent, or Firm* — Nixon & Vanderhye P.C.

(57) ABSTRACT

A ventilator (10), including: a housing (12); a reservoir (62) within the housing, wherein the reservoir has an internal chamber, an air inlet port (55), configured to place in fluid communication the internal chamber with atmospheric air outside the reservoir (62), and an oxygen inlet port (68), configured to place in fluid communication the internal chamber with a source of oxygen; and a primary blower (64) having an air inlet in fluid communication with the internal chamber of the reservoir (62), and an air outlet configured to be placed in fluid communication with an inspiration tube (26) external of the ventilator housing, wherein the internal chamber of the reservoir (62) presents a volume for gas mixing extending at least between the air inlet port, the oxygen inlet port and the primary blower air inlet, said volume being configured for allowing mixing of air entering in the reservoir via the air inlet port (55) with oxygen entering in the reservoir via the oxygen inlet port (68) before any gas reaches the primary blower air inlet.

51 Claims, 12 Drawing Sheets

Related U.S. Application Data

(60) Provisional application No. 63/219,716, filed on Jul. 8, 2021, provisional application No. 63/122,773, filed on Dec. 8, 2020.

(51) Int. Cl.
*A61M 16/08* (2006.01)
*A61M 16/10* (2006.01)
*A61M 16/20* (2006.01)

(52) U.S. Cl.
CPC ...... *A61M 16/024* (2017.08); *A61M 16/1005* (2014.02); *A61M 16/125* (2014.02); *A61M 16/205* (2014.02); *A61M 2016/0027* (2013.01); *A61M 16/0883* (2014.02); *A61M 2016/1025* (2013.01); *A61M 16/107* (2014.02); *A61M 16/209* (2014.02); *A61M 2202/0208* (2013.01); *A61M 2205/16* (2013.01); *A61M 2205/3344* (2013.01); *A61M 2205/3365* (2013.01)

(58) Field of Classification Search
CPC ............ A61M 16/1005; A61M 16/107; A61M 16/12; A61M 16/122; A61M 16/125; A61M 16/205; A61M 16/209; A61M 2016/0027; A61M 2016/1025; A61M 2202/0208; A61M 2205/16; A61M 2205/3344; A61M 2205/3365

See application file for complete search history.

(56) References Cited

U.S. PATENT DOCUMENTS

| | | | |
|---|---|---|---|
| 2002/0005197 A1* | 1/2002 | DeVries | A61M 16/20 128/204.21 |
| 2008/0173305 A1* | 7/2008 | Frater | B08B 9/023 128/204.26 |
| 2012/0006326 A1* | 1/2012 | Ahmad | A61M 16/021 128/204.22 |
| 2016/0193438 A1* | 7/2016 | White | A61M 16/026 128/204.23 |
| 2017/0028157 A1 | 2/2017 | Nitta | |
| 2020/0206452 A1* | 7/2020 | Al | A61M 16/12 |
| 2021/0316105 A1* | 10/2021 | Godara | A61M 16/12 |
| 2022/0401686 A1* | 12/2022 | Boulanger | A61M 16/0063 |
| 2024/0058563 A1 | 2/2024 | Ruppell, III et al. | |

OTHER PUBLICATIONS

Written Opinion of the ISA for PCT/US2021/062300, mailed Apr. 1, 2022, 8 pages.

* cited by examiner

AUTOMATED VENTILATOR

CROSS-REFERENCE PARAGRAPH

This application is a continuation of U.S. application Ser. No. 18/254,353, filed May 24, 2023, which is the U.S. national phase of International Application No. PCT/US2021/062300 filed Dec. 8, 2021 which designated the U.S. and claims priority to U.S. 63/219,716 filed Jul. 8, 2021, U.S. 63/122,773 filed Dec. 8, 2020, the entire contents of each of which are hereby incorporated by reference.

TECHNICAL FIELD

The present disclosure is directed generally to methods, devices, and systems for assisted ventilation and, more specifically, to an automated ventilator.

BACKGROUND

While many emergency and portable ventilators are on the market, an adequate low-cost automated ventilator with the required features to effectively support a patient with Acute Respiratory Distress Syndrome (ARDS), for example secondary to a viral infection such as COVID-19, is lacking.

COVID-19 targets the lungs and can cause complications like pneumonia and acute respiratory distress syndrome. Patients with medium to severe cases of COVID-19 require a ventilator to assist their breathing and to deliver enough oxygen to the lungs and the rest of the body. The number of COVID-19 cases requiring ventilation has overwhelmed the supply of available ventilators.

In addition, conventional ventilators require complicated circuitry and equipment to maintain safety, which increases manufacturing and operating costs. Also, such circuitry and equipment can degrade over time, thereby making it difficult to store conventional ventilators over a long period of time. The ability to store ventilators over a long period of time would have allowed for a long-term stockpile of ventilators that could have avoided the shortage experienced during the onset of the COVID-19 pandemic.

Thus, there is an urgent need for a novel automated ventilator that is simple and inexpensive to fabricate, optimized for rapid and scalable manufacturing, suitable for long term storage with minimal maintenance while stored, and safe and effective for treating a patient.

SUMMARY

One aspect of the technology may be embodied as a ventilator having a housing and an internal gas reservoir within the housing for mixing air and oxygen ($O_2$). A blower in the gas reservoir pumps a gas of just atmospheric air or a mixture of air and oxygen ($O_2$) from within the reservoir through an inspiration tube to a patient interface, e.g., a face mask, an intubation tube or tracheostomy tube attached to the patient. The reservoir may be supplied with oxygen at a relatively low pressure to provide elevated $FiO_2$ (fraction of inspired oxygen) inspiration gas settings, e.g., settings of greater than 21% oxygen, to the patient. The term "gas" includes a mixture of atmospheric air and oxygen, only atmospheric air without added oxygen, and the gas exhaled by the patient. The gas reservoir allows air and oxygen ($O_2$) to mix before the blower pumps the gas mixture to the patient. The gas reservoir may include an air inlet continuously open to receive atmospheric air. An air filter at an inlet to the gas reservoir may provide a small amount of air resistance to prevent the oxygen within the reservoir from leaking out through the inlet, especially during exhalation phases of a ventilation treatment. The continuous opening to the atmosphere ensures that the reservoir does not pressurize, such as with oxygen when the oxygen flow exceeds the air inlet flow to the reservoir.

The ventilator may use two blowers to provide the inspiration and exhalation functions. The first blower is a primary (or main) blower that is the above-described blower in the reservoir. The primary blower pumps a gas, e.g., atmospheric air or a mixture of air and oxygen, to the patient. The primary blower is limited so that it is not capable of generating a flow rate or pressurizing the gas to a level that may cause barotrauma to the patient. Thus, safety pressure relief valves and other pressure safety controls are not needed. In addition, during exhalation, the primary blower provides a pilot pressure to an exhalation valve to close the exhalation passage during inspiration.

The second blower is a secondary blower and may be a PEEP blower. The secondary blower provides pilot pressure to the exhalation valve during exhalation. The pilot pressure from the secondary blower ensures that the exhalation valve closes if exhalation gas pressure drops below a desired positive end-expiratory pressure (PEEP). PEEP keeps the patient's lungs inflated at a minimum pressure keeping alveoli open.

The advantages of a two blower system, e.g., the primary blower 64 and the secondary blower 128 described herein, include: a simple, inexpensive and low power arrangement to provide inspiration gas and to provide a pilot pressure that controls an exhalation valve. The two-blower system with the exhalation valve minimizes the gas leaks during exhalation and facilitates the use of a low flow oxygen source to provide oxygen. In comparison, passive exhalation valves with parabolic leaks result in extremely high oxygen utilization due to the flows required to maintain PEEP in the face of the leak.

The ventilator may include low power components, such as blowers with impellers, low power processors and displays, e.g., liquid crystal display, and avoid high power components such as compressors and cooling systems. An embodiment of the invention, the CorVent RESPOND 19™ ventilator consumes as little as 20 watts at nominal operation and a maximum of 50 watts at peak power consumption with a mean airway pressure of 28 $cmH_2O$. The low power consumption enables multiple ventilators to be attached to a single AC socket in an emergency situation. For instance, a 13 amp wall socket in Europe (230 VAC) could, in theory, carry 60 ventilators, which would allow hospitals to quickly respond to emergency situation.

The ventilator may include a fan in the housing that continually exhausts gas leaks from the housing. The fan exhausts gas from regions within the housing that are outside of the reservoir. The fan ensures that the oxygen levels in the housing do not exceed safe levels under fault conditions. For example, the oxygen supplied to the reservoir in the ventilator housing may be provided at a rate no greater than 15 liters per minute (Lpm). The fan may exhaust gas from the housing at a rate of at least 400 Lpm. The fan exhaust rate is greater than the oxygen supply rate by more than an order of magnitude. In the event of an oxygen leak at 15 Lpm into the housing, the fan prevents the oxygen ($O_2$) from rising above 25% $O_2$ which is considered an enriched oxygen ($O_2$) environment.

The ventilator uses flow sensors at the outlet of the primary blower and near the user interface and at entry to the patient's airway measuring both inspired and expired flow and volumes. The first flow sensor near the primary blower outlet measures flow and/or flow volume of the gas mixture discharged by the primary blower. The measured flow and/or volume are used as feedback to control the impeller speed of the primary blower to ensure that the inspiration gas pressure and/or flow volume actually discharged by the primary blower match the designed inspiration volumes expected by the user or set by a control algorithm executed by the ventilator. The second flow sensor near the patient interface measures the flow and/or flow volume being inhaled and/or exhaled by the patient. The second flow sensor may be used to detect when the patient begins to exhale or inhale. Such detection is used to switch the primary blower and associated valves from an inspiration phase to an exhalation phase or vice-versa.

Further, the first and second flow sensors together may be used to calculate a loss of mixed gas between the primary blower outlet and the patient. The calculated loss of mixed gas may be used to adjust the primary blower impeller speed or the period during which the primary blower generates an inspiration flow to ensure that the inspiration flow and/or pressure reaching the patient is at a level(s) set by the user or calculated by the controller for the ventilator.

The ventilator may include a failsafe sensor or communication interface such as the flow sensors, membrane panel etc. For example, the first and second flow sensors may be subject to a failure mode in which they "latchup". "Latchup" is a concern for all sensors based on CMOS technology due to undershoots and overshoots of allowed voltage ranges of signal especially if they are located external to the housing. "Latchup" refers to short circuit formed between power and ground rails in an integrated circuit (IC) leading to high current and damage to the IC. In CMOS transistors, latch up is the phenomenon of low impedance path between power rail and ground rail due to interaction between parasitic p-n-p and n-p-n transistors. A "latchup" of the flow sensor(s) may occur due to a ground bounce during an electrostatic discharge (ESD), such as a nearby lightning strike, or due to electromagnetic interference (EMI) due to a nearby, high-powered medical device. The controller for the ventilator is programmed to detect a "latchup" condition in either or both of the first and second flow sensors or any such interface. The detection may be the controller sensing that communication signals from one or both of the flow sensors or other such interface is lost by the controller. Once the controller detects that a flow sensor or other interface has latched up, the controller acts to cause all power to the sensor, interface, or all flow sensors to be stopped and thereafter, such as after five to ten seconds, applies power to allow the sensor(s) to reboot and reset the "latchup" condition.

The ventilator may be designed for long duration stock pile storage, such as for periods of one to several years, without maintenance or with minimal maintenance. The housing of the ventilator may be rectangular with generally flat sides, front and back panels. The rectangular shape of the housing allows many ventilators to be stacked during storage. To allow for long term storage, the ventilator may not include batteries, chemical based oxygen sensors, or pressure and flow sensors that require frequent calibration.

To avoid the need for oxygen sensors, the primary blower with reservoir and fan in the housing ensure that under no circumstance oxygen levels associated with the ventilator rise to unsafe levels.

The flow sensors may be based on CMOS technology with low drift rates which does not require yearly calibrations.

A valve(s), such as a solenoid valve or other electrically activatable valve, may be used for switching between inspiration and exhalation phases. A solenoid or other electrically activatable valve ("solenoid valve" herein) requires minimal maintenance and are suited for long term storage. A solenoid valve may be used as the exhalation valve in the ventilator. The secondary blower may provide a pilot PEEP pressure to the valve.

One aspect of the technology may be embodied as a ventilator, including: a housing; a reservoir within the housing, wherein the reservoir has an internal chamber, an air inlet port, configured to place in fluid communication the internal chamber with atmospheric air outside the reservoir, and an oxygen inlet port, configured to place in fluid communication the internal chamber with a source of oxygen; and a primary blower having an air inlet in fluid communication with the internal chamber of the reservoir, and an air outlet configured to be placed in fluid communication with an inspiration tube external of the ventilator housing, wherein the internal chamber of the reservoir presents a volume for gas mixing extending at least between the air inlet port, the oxygen inlet port and the primary blower air inlet, said volume being configured for allowing mixing of air entering in the reservoir via the air inlet port with oxygen entering in the reservoir via the oxygen inlet port before any gas reaches the primary blower air inlet.

Another aspect of the technology may be embodied as a ventilator comprising: a housing; a reservoir within the housing including an air inlet open to receive atmospheric air, an oxygen inlet port to receive oxygen from a flow delivery source of oxygen, wherein the reservoir has an internal chamber open to the air inlet and the oxygen inlet; and a primary blower having a gas inlet in fluid communication with the internal chamber of the reservoir, and an outlet configured to be in fluid communication with an inspiration tube external of the ventilator housing, wherein a volume of the internal chamber is at least as great as two liters, and preferably between two and four liters, between 2.3 and 2.9 liters, between 2.3 and 2.6 liters, or at 2.5 liters.

The ventilator may include a three (3) port two (2) way exhalation valve having exhalation gas flow passage, a pilot pressure chamber and a diaphragm between the exhalation gas flow passage and the pilot pressure chamber, wherein the diaphragm moves between opening the exhalation gas flow passage and closing the exhalation gas flow passage depending on a pressure difference between the pressure of the exhalation gas flowing through the exhalation gas flow passage and a pressure in the pilot pressure chamber.

The ventilator may include a pneumatic shunt to compensate for occlusion in an exhalation passage. The shunt is a passage between inhalation and exhalation passages. The shunt includes a one-way valve to allow gas to flow from the inhalation passage, such as from a port near the blower exhaust, to a port in a distal portion of the exhalation passage. The one-way valve opens when pressure in the exhalation passage exceeds a threshold level based upon pressure and time corresponding a blockage in the exhalation passage. The shunt prevents an excessive pressure buildup in the exhalation passage which can cause an excessive pressure in the inhalation passage or prevent the patient from exhalation.

The ventilator may operate in a blower mode if a failure occurs in one or more of the flow or pressure sensors. These sensors detect gas flow and/or pressures in the inhalation and exhalation passages. Data from the sensors are used to control the speed of the blower. In the event of a sensor failure and/or data is otherwise unavailable (or unreliable)

from the sensors, the ventilator automatically switches to a blower mode in which the primary blower is operated to run a predefined speed (RPM) of the impeller. This predefined speed corresponds to a desired exhalation flow pressure.

The ventilator may include an oxygen mixing system configured to adjust oxygen level in the gas mixture delivered to patient. The amount of oxygen delivered to the reservoir is regulated by a solenoid valve that cyclically turns on and off the oxygen flow into the reservoir. The cycle of on/off is determined by a controller based on a user inputted desired percentage of oxygen in the gas mixture flowing to the patient and the volume of gas exiting the blower. For higher oxygen levels, the solenoid valve opens to allow more oxygen to flow into the reservoir during each cycle. The portion of the period of the cycle that the solenoid valve is open is used to control the amount of oxygen flowing into the reservoir and thus the oxygen levels in the gas mixture pumped by the primary blower to the patient.

Another aspect of the technology may be embodied as a ventilator comprising: a primary blower having an air inlet and an air outlet, wherein the primary blower gas outlet is configured to be placed in fluid communication with an inspiration tube to ventilate a patient, a PEEP blower having an air inlet and an air outlet, and an exhalation valve including an exhalation flow passage having an inlet configured to be placed in fluid communication with an exhalation tube receiving exhaled gases from the patient and an outlet in fluid communication with an exhalation exhaust that exhausts gas from the ventilator; wherein the ventilator is configured to switch between an inspiration phase, during which the exhalation valve closes the exhalation flow passage, and an exhalation phase, during which the exhalation valve opens the exhalation flow passage; wherein during the inspiration phase, the exhalation valve is configured to receive a first pilot pressure from the primary blower and close the exhalation flow passage; and wherein during the exhalation phase, the exhalation valve is configured to receive a second pilot pressure from the PEEP blower and to maintain open the exhalation flow passage while a pressure in the exhalation flow passage is above a set PEEP pressure and to close the exhalation flow passage if the pressure in the exhalation flow passage is below the set PEEP pressure.

Another aspect of the technology may be embodied as a ventilator comprising: a primary blower having an gas inlet and an gas outlet, wherein the primary blower gas outlet is configured to be placed in fluid communication with an inspiration tube to ventilate a patient, an exhalation valve including an exhalation flow passage having an inlet configured to be placed in fluid communication with an exhalation tube receiving exhaled gases from the patient and an outlet in fluid communication with an exhalation exhaust that exhausts gas from the ventilator, wherein the ventilator is configured to switch between an inspiration phase, during which the exhalation valve closes the exhalation flow passage, and an exhalation phase, during which the exhalation valve opens the exhalation flow passage; and wherein the exhalation valve comprises: an opening in the wall of the exhalation flow passage allowing fluid communication between the inlet and the outlet of the exhalation flow passage, a selecting element selectively movable between a closed position, wherein it closes the opening in the wall of the exhalation flow passage and prevents passage of gas through the exhalation flow passage and an open position, wherein it leaves said opening in the sidewall open and allows passage of air through the exhalation flow passage.

Another aspect of the technology may be embodied as a ventilator comprising: a primary blower configured to pump inspiration gas, during an inspiration phase of the ventilator, to an inspiration tube connectable to ventilate a patient; an exhalation valve including an exhalation flow passage having an inlet in fluid communication with an exhalation tube that receives exhaled gases exhaled by the patient and an outlet in fluid communication with an exhalation exhaust that exhausts the breath from the ventilator; the exhalation valve switches between the inspiration phase during which the exhalation valve closes the exhalation flow passage and an exhalation phase during which the exhalation valve opens the exhalation flow passage; during the inspiration phase, the exhalation valve receives a pilot pressure from the primary blower and closes the exhalation flow passage to suppress gas movement through the exhalation tube, and during the exhalation phase, the exhalation valve receives the pilot pressure from a PEEP blower which maintains open the exhalation flow passage while a pressure in the exhalation flow passage is above a PEEP pressure and closes the exhalation flow passage if the pressure in the exhalation flow passage is below the PEEP pressure and the primary blower switches to controlling the blower pressure at or just below the PEEP pressure.

The exhalation valve may include a diaphragm, wherein a first surface of the diaphragm is exposed to the pilot pressure in the pilot pressure chamber and a second surface is exposed to the exhaled gases in the exhalation flow passage, and an area of the first surface is greater than an area of the second surface such as by a factor of between 1.5 and 4, between 1.7 and 2.4 or a factor of 2.

Another aspect of the technology may be embodied as a ventilator comprising: a primary blower configured to pump an inspiration gas through an inspiration port which is connectable to an inspiration tube which conveys the inspiration gas to a patient being ventilated; an exhalation port connectable to an exhalation tube configured to receive exhalation gas exhaled by the patient; an exhalation exhaust; an exhalation valve including an exhalation flow passage having an inlet in fluid communication with the exhalation port and an outlet in fluid communication with the exhalation exhaust, a pilot pressure chamber and a diaphragm separating the pilot pressure chamber from the exhalation flow passage, and a PEEP blower configured to provide a pilot pressure proportional to a PEEP pressure level; wherein, during an inspiration phase of the ventilator, the pilot pressure chamber is pressurized by the primary blower to deflect the diaphragm to close the exhalation flow passage to the closed position to prevent gas flow through the exhalation port during the inspiration phase, and during an exhalation phase of the ventilator, the pilot pressure chamber is pressurized by the PEEP blower which causes the diaphragm to deflect to open the exhalation valve while the exhalation gas is above the PEEP pressure level and deflect to close the exhalation flow passage while the exhalation gas is below the PEEP pressure level while the primary blower switches to controlling the blower pressure at or just below the PEEP pressure during the exhalation phase.

Another aspect of the technology may be embodied as a tubing assembly to be attached to a housing of a ventilator, the tubing assembly including: an inspiration tube including an inlet connectable to an inspiration port of the housing; an exhalation tube including an outlet connectable to an exhalation port of the housing; a coupling device configured to connect to a mask or intubation device, and having a flow passage for gas flow between the mask or intubation device and the inspiration tube and the exhalation tube; a one-way valve connected to an outlet of the inspiration tube and in fluid communication with the coupling device, wherein the one-way valve is configured to allow inspiration gas to flow from the inspiration tube into the coupling device and block flow from the coupling device into the inspiration tube, and wherein the one-way valve is configured to allow exhalation gas to flow from the coupling device into the exhalation tube and block flow from the exhalation device into the coupling device.

Another aspect of the technology may be embodied as a tubing assembly to be attached to a housing of a ventilator, the tubing assembly including: an inspiration tube including an inlet connectable to an inspiration port of the housing; an exhalation tube including an outlet connectable to an exhalation port of the housing; a coupling device configured to connect to a mask or intubation device, and having a flow passage for gas flow between the mask or intubation device and the inspiration tube and the exhalation tube; a one-way valve connected to an outlet of the inspiration tube and in fluid communication with the coupling device, wherein the one-way valve is configured to allow inspiration gas to flow from the inspiration tube into the coupling device and block flow from the coupling device into the inspiration tube, and wherein the one-way valve is configured to allow exhalation gas to flow from the coupling device into the exhalation tube and block flow from the exhalation device into the coupling device.

BRIEF DESCRIPTION OF THE DRAWINGS

For an understanding of embodiments of the disclosure, reference is now made to the following description taken in conjunction with the accompanying drawings, in which.

DETAILED DESCRIPTION

Figure 1:
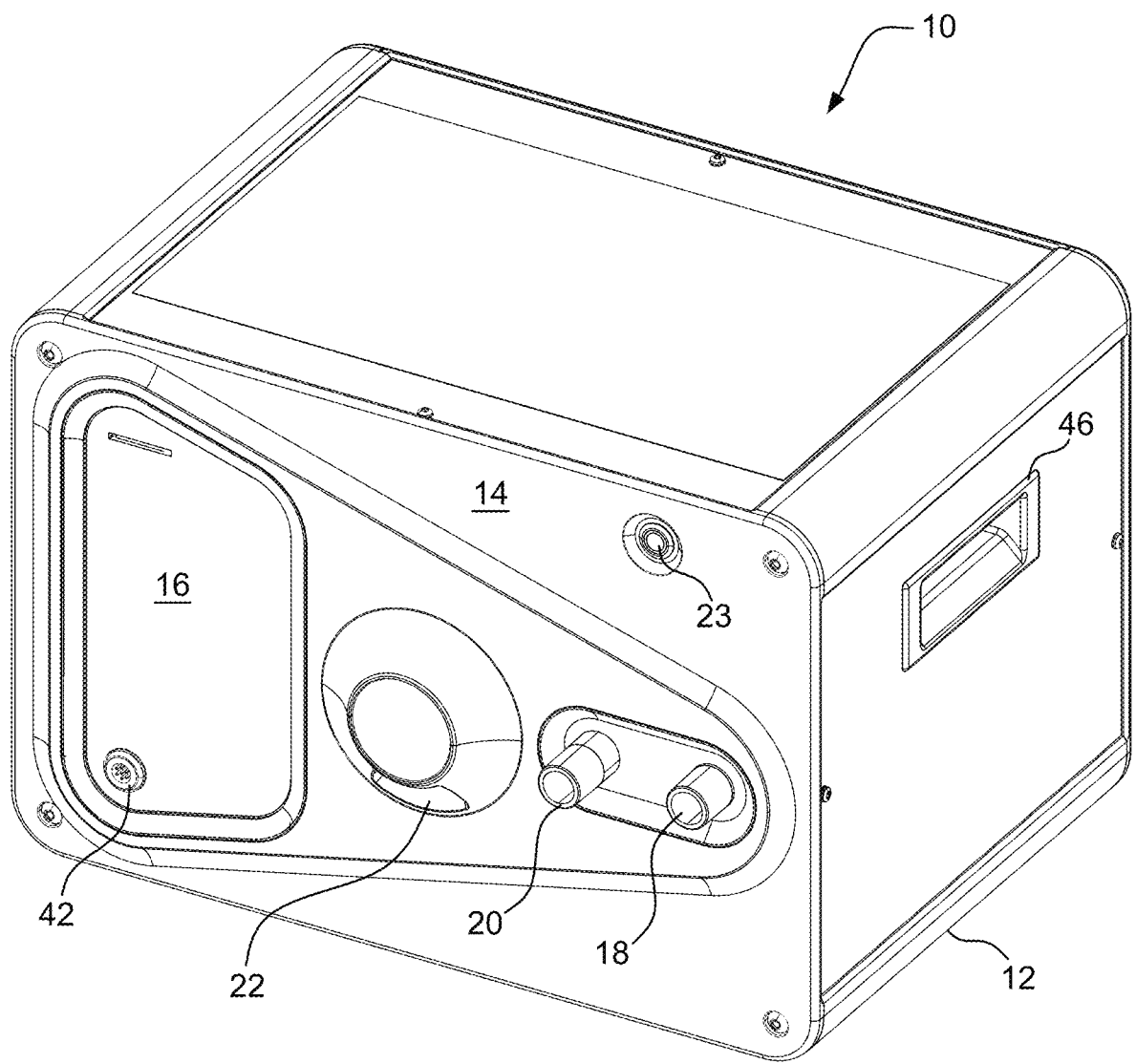
FIG. 1 is a front perspective view of an automated portable ventilator in accordance with an exemplary embodiment.
Figure 2:
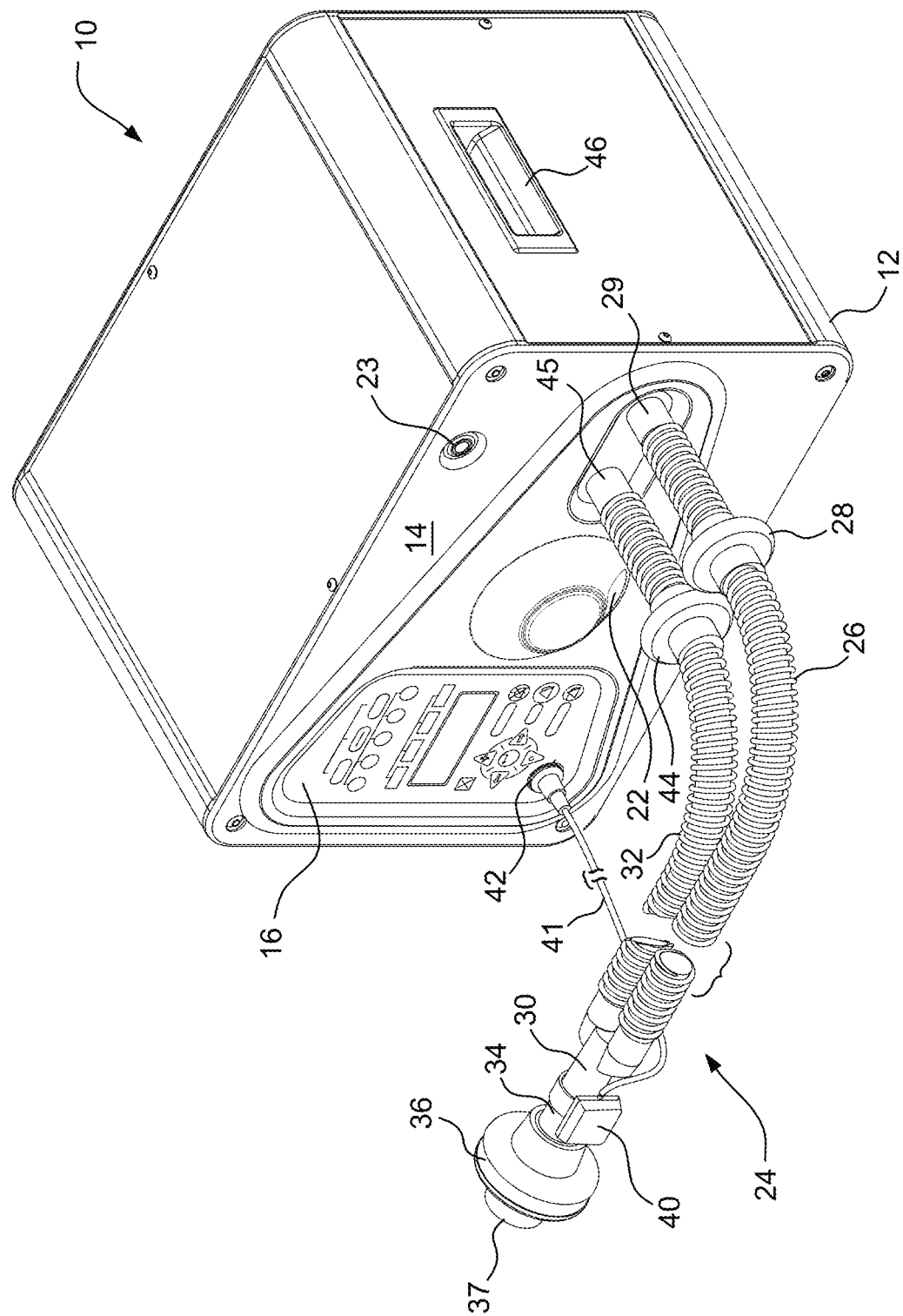
FIG. 2 is another front perspective view of the ventilator with a detachable and disposable tubing assembly including inspiration and exhalation flow passages.
Figure 3:
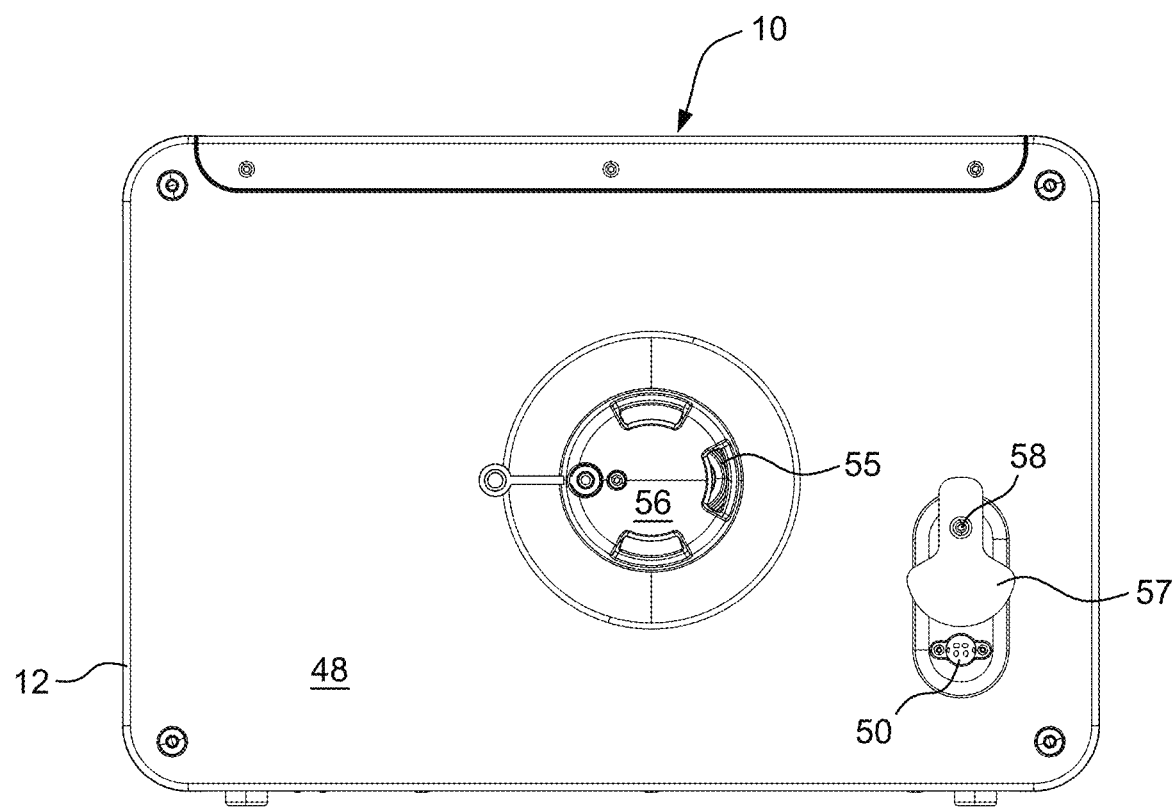
FIG. 3 is a rear view of the ventilator showing a rear panel of the ventilator.

FIGS. 1 to 3 show an automated portable ventilator 10 including a housing 12 with a front panel 14 having a user interface 16 (which may include a display), an inspiration port 18 for inspiration air being pumped to the patient, an exhalation port 20, an exhalation exhaust 22, and a run/standby switch 23 that is used for entering or exiting "ventilation" mode.

FIG. 2 shows a tubing assembly 24 which is releasably attached to the housing 12. The tubing assembly 24 includes an inspiration portion that includes an inspiration tube 26, a gas filter 28 (e.g., a bacterial and virus filter) coupled to the inspiration tube 26, and a coupling 29 for connecting the inspiration tube 26 and/or filter 28 to the inspiration port 18 of the housing 12. An outlet end of the inspiration tube 26 attaches to a first port of a Y-junction coupling 30. A second port of the Y-junction 30 connects to an inlet of an exhalation tube 32. A third port of the Y-junction 30 joins a connection tube 34, which connects to a user ventilation device such as a face mask or an intubation tube. A heat and moisture exchanger (HME) 36 may be optionally coupled to the connection tube 34 using conical fittings (or other coupling devices). A coupling device 37 is at the distal end of the connection tube 34 or HME 36. The coupling device 37 connects to the face mask or intubation device 38 (FIG. 6) mounted to the patient.

A flow sensor 40 may be connected to the connection tube 34. The flow sensor 40 collects flow data regarding the gas flow rate, timing and direction of the gas flow passing through the connection tube 34, such as gas flow into and out of the patient. The proximity of the flow sensor 40 to the patient ensures that the flow data accurately indicates the breathing conditions of the patient, such as when the patient initiates inhalation and exhalation, and the volume and/or gas flow rate of the gas being inhaled and exhaled by the patient.

A communication cable 41 transmits the data collected by the flow sensor 40 to a data link connection 42 on the front panel 14 of the housing 12 of the ventilator 10. The data from the flow sensor 40 may alternatively be transmitted wirelessly and thereby avoid the need for the communication cable 41.

The outlet end of the exhalation tube 32 may include an air filter 44 to ensure that viruses and bacteria from the patient do not enter the housing 12 of the ventilator 10. In addition, the exhalation tube 32 may be connected to the exhalation port 20 of the housing 12 by a coupling 45. Exhaled gas passes from the exhalation tube 32, into the exhalation port 20, through tubing in the housing 12 and out the exhalation exhaust 22 on the front panel 14 of the ventilator housing.

The tubing assembly 24 may be an integrated assembly of components of inspiration and exhalation tubing 26, 32, air filters 28, 44, the Y-junction 30, the flow sensor 40, the connection tube 34, and/or the HME 36. The patient coupling device 37 may or may not be part of the integrated assembly. The integrated assembly may be manufactured to form a single piece, disposable unit that is attachable to the housing 12 of the ventilator 10.

The filters 28, 44 in the tubing assembly 24 ensure that bacteria and viruses are not transmitted from the ventilator 10 into the patient and are not transmitted from the patient through the exhalation exhaust 22 and into the air where health care professionals are working.

As shown in FIG. 3, the housing 12 of the ventilator 10 may be generally rectangular with substantially flat panels for the front 14 (FIG. 2), as well as side, top, bottom and rear panels. The rectangular, flat shape of the panels for the ventilator 10 allows the ventilator to be stacked with other ventilators 10 for storage. Recessed handles 46 (FIG. 2), on the side panels of the housing allow a person to easily grasp and move the ventilator.

The housing 12 may be formed in a rectangular cuboid shape and configuration with each panel having a rectangular shape, although other shapes and configurations such as, but not limited to, circular or oval are contemplated to be within the scope of the disclosure. The rectangular cuboid shape and configuration allows for multiple ventilators to be stacked on top of one another for storage, transportation, and stock piling purposes. The ventilator 10 may be light weight, such as no more than fifteen (15) pounds. The light weight allows one person to carry the ventilator from storage to a location near a patient.

Figure 7:
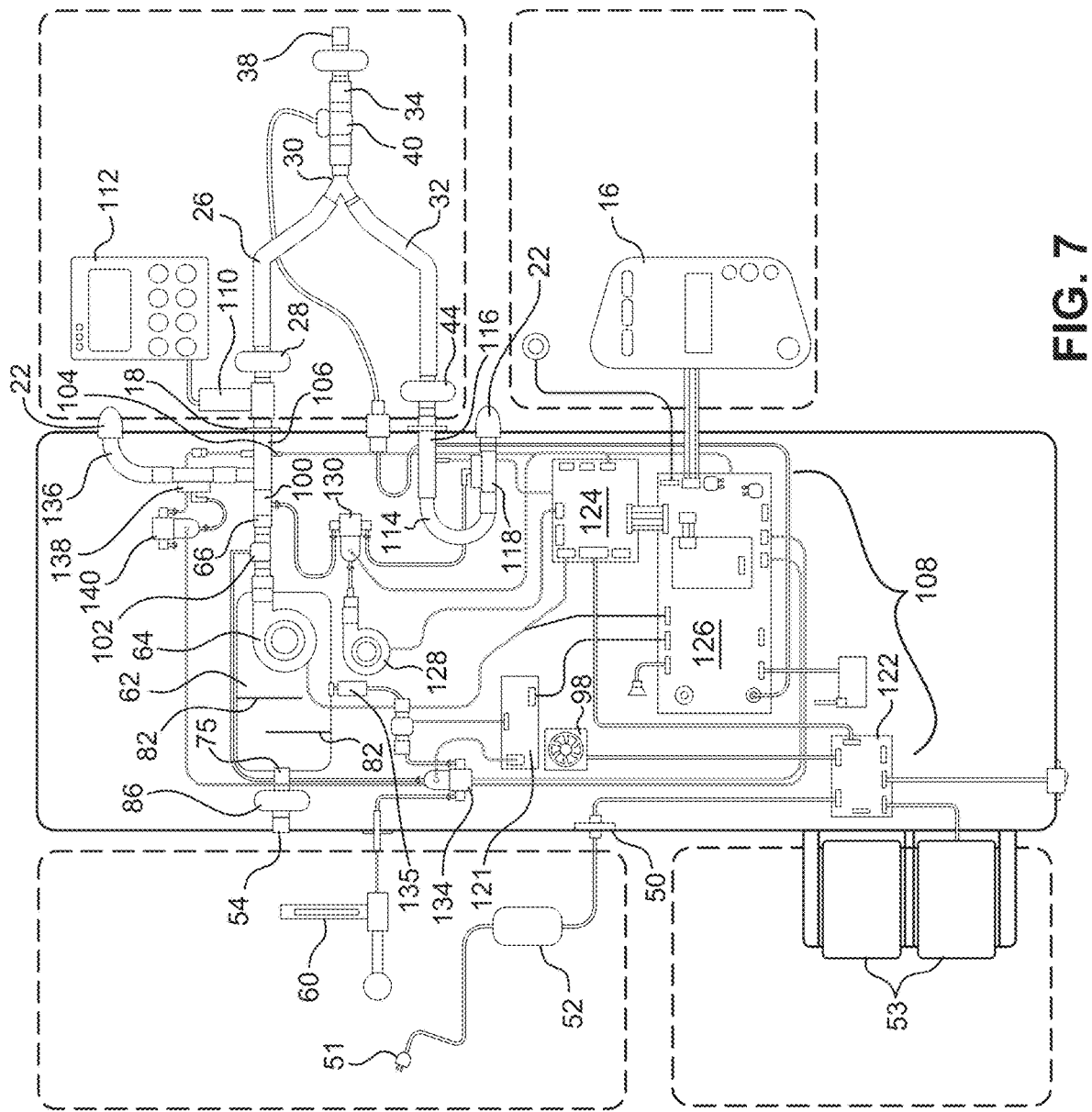
FIG. 7 is a schematic diagram of the pneumatic and electronic components of the ventilator.

As shown in FIG. 3, the rear panel 48 includes an electric power connection 50 connectable to an external power source 51 (FIG. 7). The power connection 50 may include an AC/DC converter and transformer 52. The power source may be a low-voltage DC (direct current) source such as a source of 24 volts DC. The power source may include a battery 53, such as a back-up battery supply. The power source may also receive electrical power from a conventional source such as 120/240 volts of AC current. A power switch 54 (FIG. 4) on the rear panel 48 is used to turn the ventilator 10 on or off and may be recessed to avoid inadvertently turning the ventilator 10 on or off.

The combination of run/standby switch 23 and the power switch 54 may act as a safety feature. In particular, the user may be prevented from actuating the power switch 54 to turn the ventilator 10 off (i.e., terminate power to the ventilator) before the run/standby switch 23 is set to "standby" mode. In "standby" mode, the primary blower 64 and a secondary blower 128 (e.g., a blower configured as a PEEP blower) are shut down so that ventilation is turned off. Once the ventilator 10 is in "standby" mode, the power switch 54 may be actuated to turn off the ventilator 10. If the user actuates the power switch 54 to turn off the ventilator 10 before setting the ventilator 10 to "standby" mode, an alarm may sound. It is also contemplated that the power switch 54, the run/standby switch 23, and/or the ventilator 10 as a whole may be configured so that the user cannot turn off the ventilator before setting the ventilator to "standby" mode. Preventing the ventilator 10 from being shut down before being set to "standby" mode may prevent damage to the components of the ventilator 10 and/or damage to the patient. It is contemplated that the ventilator 10 may also include a cover 57 that covers the power switch 54 to prevent inadvertent actuation of the power switch 54. For example, the cover 57 may be rotated to an uncover position that allows access to the power switch 54 and may be rotated back to a cover position that prevents access to the power switch 54.

An atmospheric air inlet port 55 may be always open and covered by a shield 56 displaced from the flat surface of the rear panel 48 to prevent a blockage of atmospheric air entering the port. An outer oxygen ($O_2$) inlet port 58 on the rear panel 48 is connectable to a source 60 (FIG. 7) of pure oxygen ($O_2$) such as a portable oxygen tank or to an oxygen distribution source in a hospital. The oxygen source 60 may be a low flow and/or pressure source providing oxygen in a range of 10 to 20 liters per minute (Lpm) or up to 15 Lpm. The outer oxygen inlet port 58 may be a low flow oxygen port that restricts the flow of oxygen to 15 Lpm or less.

Figure 4:
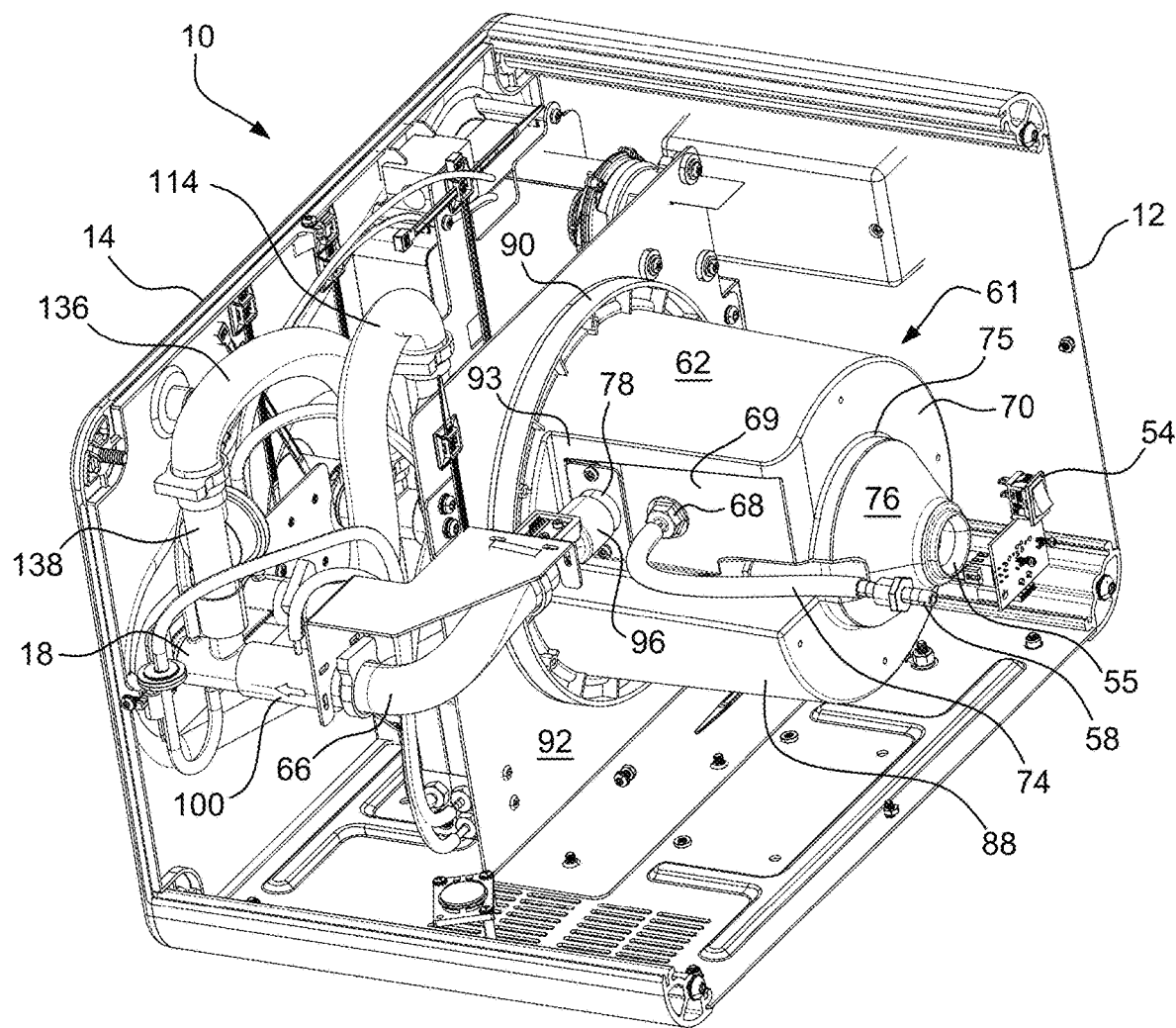
FIG. 4 is a rear and top perspective view of the ventilator with the outside panels of the housing removed except for the front panel.
Figure 5:
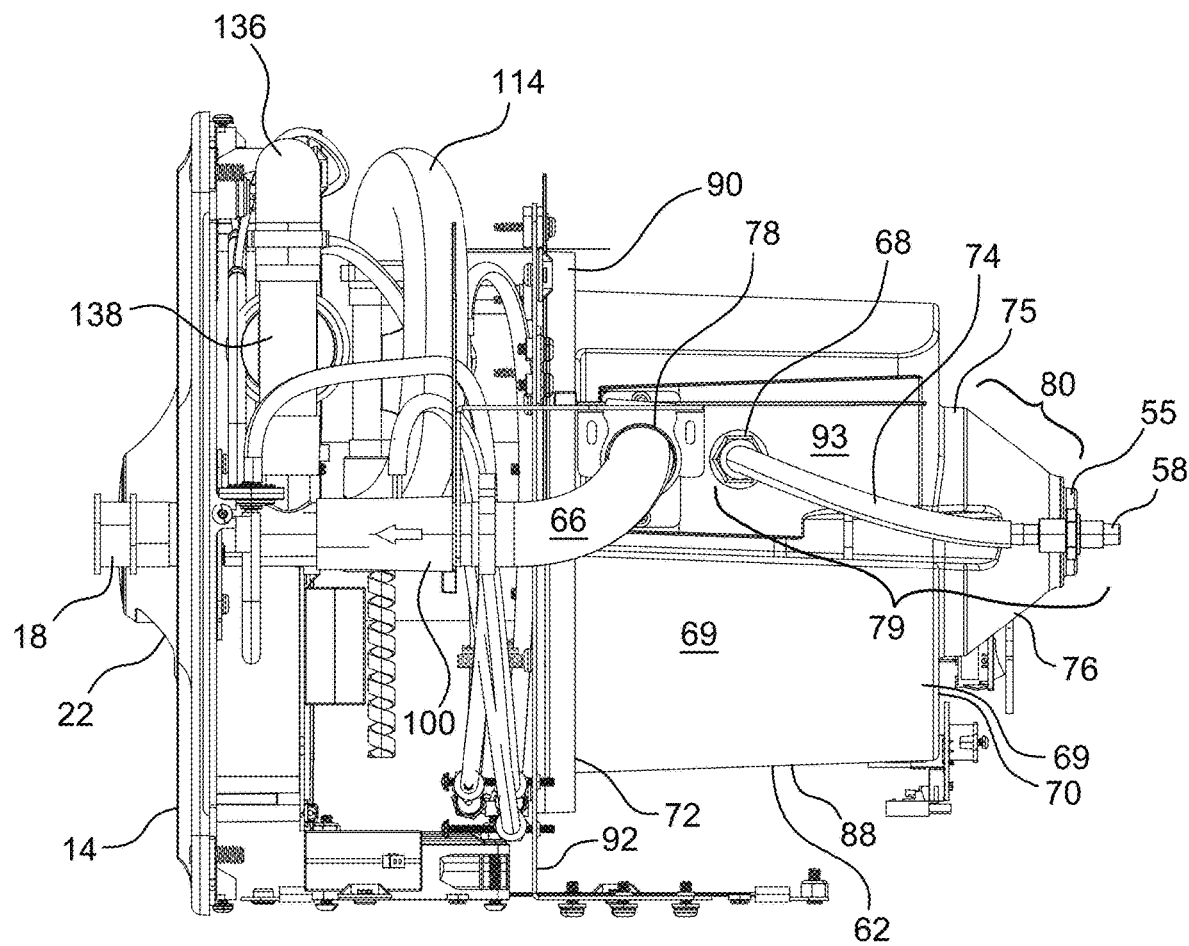
FIG. 5 is a side view of the internal components of the ventilator and the front panel.

FIGS. 4 and 5 are views of the ventilator 10 with the outside panels of the housing 12 removed (for illustrative clarity) except for the front panel 14. A blower and reservoir assembly 61 is within the housing 12 (FIG. 2). The blower and reservoir assembly 61 includes a reservoir 62 that holds a gas to be pumped to the patient as inspiration gas. The gas may be atmospheric air or a mixture of atmospheric air and oxygen ($O_2$) that is received by way of the atmospheric air inlet port 55. For example, atmospheric air may flow directly into the reservoir 62 from the atmospheric air inlet port 55, while pure oxygen may flow directly into the reservoir 62 from the outer oxygen inlet port 58. Once received in the reservoir 62, the gas is drawn from the reservoir 62 and pumped by the primary blower 64, under a pressure above atmospheric, through an outlet of the primary blower 64 and to an inspiration conduit 66 that directs the gas mixture from the primary blower 64 to the inspiration port 18.

The ventilator 10 may operate without being connected to a source 60 (FIG. 7) of oxygen ($O_2$). It is further contemplated that the flow of oxygen through the outer oxygen inlet port 58 into the reservoir 62 may be turned off during some operational conditions of the ventilator 10. Oxygen typically comprises about 21% of atmospheric air. Thus, if the patient needs inspiration gases with a concentration of oxygen greater than 21%, supplemental oxygen ($O_2$) may be added to the atmospheric air in the reservoir 62 to increase the oxygen level in the gas mixture.

One feature of the blower and reservoir assembly 61 is that the maximum pressure that can be generated by the primary blower 64 is less than the maximum inspiration pressure that is safe for a patient. These high pressures may only be generated at low flows and as a function of the construction and arrangement of the primary blower 64. Thus, the primary blower 64 can be configured as a safeguard preventing inspiration air flowing to the patient at an unsafe pressure level.

Another feature of the blower and reservoir assembly 61 is to ensure that the gas mixture pumped to the patient by the primary blower 64 does not exceed an unsafe level of $O_2$. In particular, oxygen in the ventilator 10 can present a fire risk if the concentration of oxygen leaking into chassis of the ventilator exceeds a particular level (e.g., greater than 25% of the total composition of the gas mixture).

In order to prevent the concentration of oxygen from exceeding an unsafe level, it is contemplated that the atmospheric air inlet port 55 to the reservoir 62 may be always open to allow atmospheric air into the reservoir 62. Thus, the reservoir 62 can be configured to always receive a constant supply of atmospheric air at a rate equal to the flow rate at the blower outlet minus the flow rate of supplemental $O_2$ from the outer oxygen inlet port 58 into the reservoir 62. Atmospheric air flows into the reservoir 62 due to the slight pressure reduction in the reservoir 62 caused by the primary blower 64 drawing in air and moving gas into the inspiration air conduit 66. The reservoir is sealed to be gas tight at the expected pressure levels preventing gas leakage into the chassis.

The reservoir 62 defines an internal chamber having a relatively large interior volume, such as a volume of 2 liters or 2.5 liters. It is contemplated that the internal chamber may have a volume above a threshold volume, such as a threshold volume of at least 1.5 liters, at least 2.0 liters, and/or at least 2.5 liters. The reservoir 62 can comprises a volume of at most 3 liters. The volume of the reservoir chamber is substantially larger than the volume of gases delivered to a patient during an inspiration phase, e.g., a breath. The relatively large volume of the reservoir chamber 62 minimizes ripples, i.e., variations in the concentration of oxygen in the gas (fractional inspired oxygen ($FiO_2$)) delivered to the patient's airways. The volume of the reservoir chamber 62 is also substantially larger than the volume of the air passage between the primary blower 64 and the mask or other patient interface 38 through which the gas mixture is delivered to the patient. This air passage may include the inspiration conduit 66, the inspiration tube 26, the Y-junction 30, the flow sensor 40, and the mask or intubation device 38. A large interior volume of the reservoir 62 provides a large mixing volume for oxygen and atmospheric air to mix before the mixture enters the primary blower 64 minimizing delivered $FiO_2$ ripple.

Oxygen ($O_2$) enters the reservoir 62 through an inner oxygen inlet port 68 positioned on a sidewall 69 of the reservoir 62 that is between a rear wall 70 and a front wall 72 of the reservoir 62. The inner oxygen inlet port 68 may be positioned in a region on the sidewall 69 that is centered on the middle of the sidewall 69 and has a range that is 20% the distance between the rear wall 70 and the front wall 72 so that the inner oxygen inlet port 68 can be located about equal distance between the rear wall 70 and the front wall 72, closer to the rear wall 70, or closer to the front wall 72. In addition, a conduit 74 is internal to the housing 12 and connects the outer oxygen inlet port 58 to the inner oxygen inlet port 68.

The atmospheric air inlet port 55 is at or near the rear panel 48 of the housing 12 and is connected to an inlet port 75 in the rear wall 70 of the reservoir 62 via an air passage 76. The primary blower 64 may be at or near the front wall 72. The primary blower 64 may also be housed within the front wall 72. In addition, the air inlet to the primary blower 64 is in fluid communication with the internal chamber of the reservoir 62. The inner oxygen inlet port 68 may be positioned away from the air inlet of the primary blower 64 to reduce the risk that excess oxygen will enter the primary blower 64 and be pumped towards the patient. Also, positioning the inner oxygen inlet port 68 away from the air inlet of the primary blower 64 allows the oxygen to mix with the atmospheric air in the reservoir 62 before the mixture enters the primary blower 64. The position of the inner oxygen inlet port 68 can be positioned away from the atmospheric air inlet port 55 to prevent oxygen loss from the reservoir 62 during exhalation when oxygen continues to flow.

The reservoir 62 may be hermetically sealed except for the inlet port 75, the inner oxygen inlet port 68 and an outlet 78 for the primary blower 64. Sealing the reservoir 62 reduces the risk of oxygen leaking from the reservoir 62 into other regions inside the housing 12, and aids in controlling the oxygen level in the reservoir 62.

The inner oxygen inlet port 68, conduit 74, and/or outer oxygen inlet port 58 may form an oxygen flow passage(s) 79. In addition, the inlet port 75, the air passage 76, and/or the atmospheric air inlet port 55 may form an atmospheric flow passage(s) 80. The oxygen flow passage(s) 79 may have a cross-sectional area that is substantially smaller than the cross-section area of the atmospheric flow passage(s) 80, e.g., less than 75%, 50%, 25% or 10% of the cross-sectional area of the atmospheric flow passage(s) 80.

A baffle plate(s) 82 (FIG. 7) within the reservoir 62 may form a partition which divides the internal chamber of the reservoir 62 into sections. The baffle plate(s) 82 may be supported and/or reinforced by one or more support devices to limit movement of the baffle(s) 82 due to pressure from the flow of oxygen and air in the reservoir 62. For example, the baffle plate(s) 82 may be supported by one or more posts that extend from the baffle plate(s) 82 to the rear wall 70 or to the sidewall 69. The baffle plate(s) 82 may be between the inlet port 75 and the inner oxygen inlet port 68 along an axis of the reservoir 62. The baffle plate(s) 82 may comprise a flat plastic or metal plate having an outer edge configured to abut and engage an inner side of one of the walls of the reservoir 62. The baffle plate(s) 82 includes openings to allow the atmospheric air to freely move through the baffle plate(s) 82. The openings may be arranged closer to the outer edge than to the center of the baffle plate(s) 82. The baffle plate(s) 82 can be configured to muffle noise from the primary blower 64 from emanating out of the reservoir 62 and into the area near the ventilator 10 and it aids in mixing the gas when the air is entrained. Noise is also muffled by an air filter 86 (FIG. 7) positioned within the air passage 76.

The reservoir 62 may include a bucket 88 and a base plate 90 mounted to a bracket plate 92 in the housing 12. The reservoir 62 is supported by the bracket plate 92 in the housing 12. The primary blower 64 is mounted to the base plate 90 such that the primary blower 64 is within the reservoir 62. An open generally circular edge of the bucket 88 is attached to the base plate 90 to form a seal between the bucket 88 and the base plate 90. The base plate 90 may be generally circular and includes ribs to provide structural support to the bucket 88 and the reservoir 62 and the primary blower 64. The bucket 88 may have a generally cylindrical outer wall. There may be a recessed side portion 93 of the bucket 88 to accommodate the primary blower air outlet 78, the conduit 74 and the inner oxygen inlet port 68. The recessed side portion 93 may be used to reduce the volume needed inside the housing 12.

The primary blower 64 may be mounted to the base plate 90. The primary blower 64 may include a centrifugal impeller within a cylindrical housing. The centrifugal impeller may be a single centrifugal impeller having an axial extension significantly smaller, optionally 50% or 25% or 10% smaller than its radius to provide the primary blower 64 with a thin discoidal conformation. An inlet (not shown) to the primary blower 64 faces the interior of the reservoir 62. The outlet 78 of the primary blower 64 is connected by the coupling 96 to the inspiration air conduit 66.

In operation, the primary blower air inlet receives the gas from the interior of the reservoir 62. The gas in the reservoir 62 comes as atmospheric air through inlet port 75 and as oxygen entering through the inner oxygen inlet port 68. Atmospheric air enters at a far end of the reservoir 62 and moves through the interior of the reservoir 62 and through the baffle plate 82. The atmospheric air is drawn through the reservoir 62 by the suction created at the primary blower air inlet 94. The oxygen, if present, enters the reservoir 62 through the inner oxygen inlet port 68 and mixes with the atmospheric air in the reservoir 62. The oxygen and atmospheric air are well mixed when they reach the primary blower 64.

The sound of the primary blower 64 is suppressed by the baffle plate 82 before the sound emanates through the atmospheric air inlet port 55. The sound of the primary blower 64 is also suppressed due to a filter 86 at the atmospheric air inlet port 55 to the internal chamber of the reservoir 62. The baffle plate 82 and filter 86 may suppress the sound of the primary blower 64 by five (5) decibels. It is contemplated that the baffle plate 82 and filter 86 may suppress the sound of the primary blower 64 by at least two (2) or three (3) decibels.

The relatively large volume of the reservoir 62, the continuously open atmospheric air inlet port 55 and the separation between the primary blower 64 and the inner oxygen inlet port 68 ensure that the mixture of gases reaching the primary blower 64 has an oxygen concentration below levels that pose risks such as fire.

The blower and reservoir assembly 61 are supported by the bracket plate 92 within the housing 12. The bracket plate 92 may have an L-shape with a narrow foot mounted to a bottom panel of the housing 12 and a leg panel supporting the base plate 90 of the reservoir 62.

A fan 98 (FIG. 7) may be mounted to the bottom panel of the housing 12 such that gases within the housing 12 are exhausted through the bottom panel to atmospheric air. The fan 98 continually moves gases from the housing 12 to atmospheric air. The fan 98 ensures that any build-up of oxygen in the housing 12 is exhausted from the housing 12 before a level of oxygen in the housing 12 becomes excessive, such as above 20 percent of the total volume of gas in the housing 12. Atmospheric air may enter the housing 12 through several designated vent openings. The flow rate of the fan 98 may be, for example, at least 40 liters per minute and/or at most 400 liters per minute while the oxygen flow rate from the oxygen source 60 may be less than 20 Lpm. Because the flow rate from the fan 98 is substantially, e.g., at least 20% greater, than the oxygen flow rate, the fan 98 will exhaust gases from the housing 12 at a greater rate than oxygen enters the housing 12.

The mixture of atmospheric air and oxygen pumped by the primary blower 64 flows through the primary blower air outlet 78, through the inspiration conduit 66, through the inspiration port 18 and into the inspiration tube 26. The inspiration conduit 66 may include a one-way-valve 100, a flow sensor 102, a pressure tap 104, and a pressure sensor 106. The proximity of the pressure sensor 106 and the flow sensor 102 to the primary blower 64 allows these sensors to collect data of the gas conditions at the primary blower air outlet 78, such as data related to gas pressure and/or flow rate. The pressure and flow rate may be used by a controller 108 (FIG. 6) of the ventilator 10 to adjust the rotational speed of the impeller of the primary blower 64 to match the actual gas mixture pressure and/or flow rate to a desired pressure and/or flow rate.

The one way valve 100 prevents air from the exhalation tube 32 from entering the primary blower 64. The one way valve 100 allows gas to flow through the inspiration tube 26 into the connection tube 34 and to the patient during the inhalation phase. Additionally, the one way valve 100 prevents gas exhaled by the patient flowing into the primary blower 64 from the inspiration tube 26. The one-way valve 100 can also be configured to minimize the amount of exhaled air from the patient entering the inspiration tube 26 by effectively closing an end of the inspiration tube 26 during the exhalation phase. By minimizing the exhaled breath entering the inspiration tube, the one-way valve minimizing the exhaled breath that is inhaled during a subsequent inspiration phase.

An oxygen sensor 110 (FIG. 7) may be in the inspiration gas passage between the inspiration port 18 and the filter 28. The oxygen sensor 110 generates data indicative of an oxygen level in the inspiration gas. An oxygen monitor 112 may be configured to analyze the data from the oxygen sensor 110 to determine the oxygen level, e.g., the $FiO_2$ level, of the inspiration gas. The oxygen monitor 112 may output information regarding the oxygen level to a display (e.g., of the user interface 16 described herein) that is read by a health care professional. The oxygen level information may also be used by the controller 108 to adjust a flow of oxygen into the reservoir 62, such as by turning on or off the flow of oxygen, or by regulating the flow of oxygen.

During operation, exhaled air from the patient passes through the exhalation tube 32 and enters the housing 12 through the exhalation port 20 on the front panel 14. After the exhaled air passes through the exhalation port 20, the exhaled air enters an exhalation conduit 114 that directs the exhaled air and other gases to the exhaust 22 on the front panel 14. The exhalation conduit 114 may include a pressure sensor 116 and an exhalation valve 118 that opens or obstructs the exhalation conduit 114 depending on whether the ventilator 10 is in an inspiration phase, wherein the valve 118 is closed, or in an exhalation phase, wherein the valve 118 is open.

Figure 6:
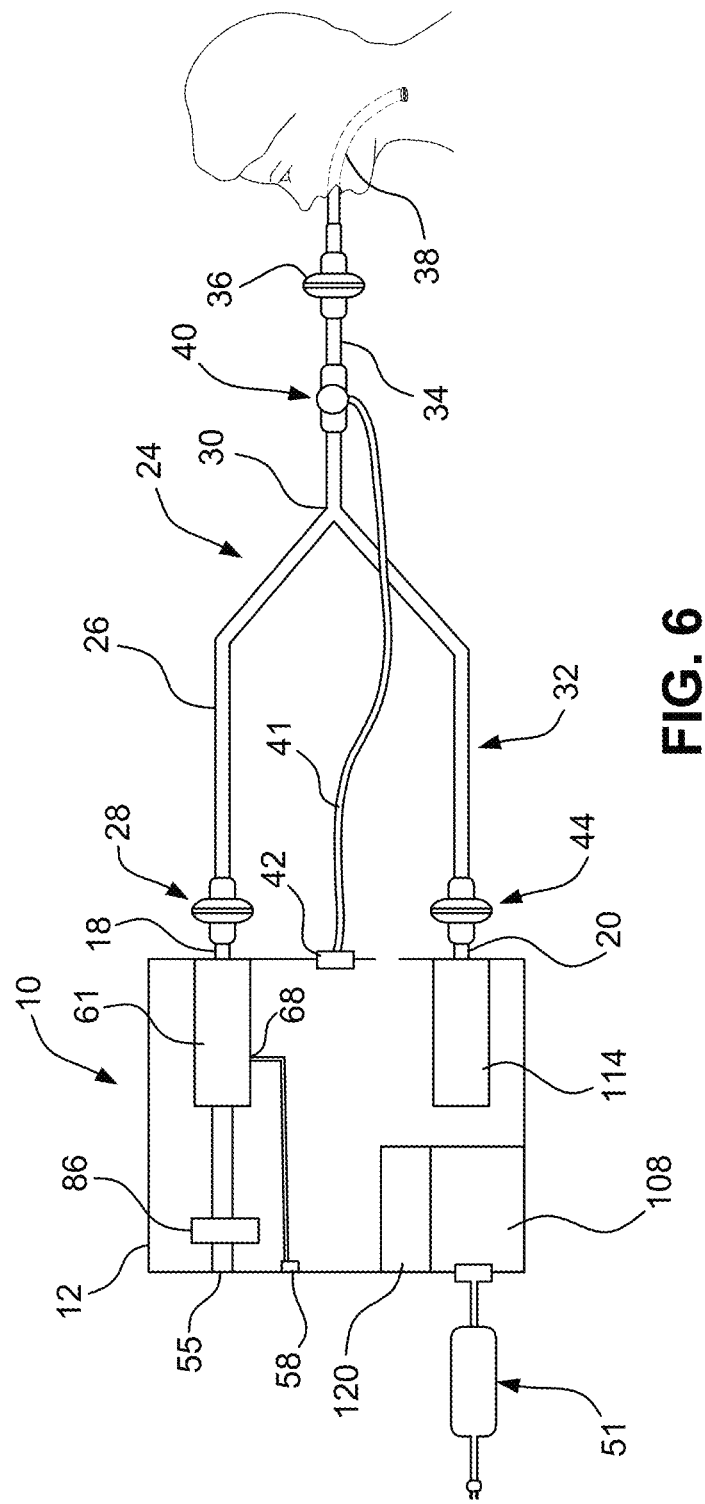
FIG. 6 is a schematic diagram of the pneumatic components of the ventilator.

FIG. 6 is a schematic diagram of the ventilator 10 including a patient coupling device 37 (FIG. 2) that connects to a mask or intubation tube 38 applied to a patient. The inspiration tube 26 is coupled to the air inspiration port 18 and the exhalation tube 32 is coupled to the air exhalation port 20. The inspiration air filter 28 is included in the inspiration tube 26 near the inspiration port 18 at the ventilator housing 12. Similarly, air filter 44 is included in the exhalation tube 32 near the air exhalation port 20 at the ventilator housing.

The filters 28, 44 prevent contaminates, such as bacteria and/or viruses, from entering the inspiration tube 26 and flowing into the patient, and these filters prevent bacteria and viruses from entering the ventilator through the exhalation tube 32. Although gas flow does not enter the ventilator housing 12 through the inspiration tube 26 during any phase of operation of the ventilator 10, the filter 28 is included to prevent bacteria and viruses from entering the ventilator 10 via the inspiration tube 26. Because the tubing assembly 24 of the patient circuit prevents bacteria and viruses from entering the ventilator housing 12, the housing 12 is not contaminated with bacteria and viruses that may be present in the breath of the patient.

The filter 86 at the atmospheric air inlet port 55, and the baffle plate 82 within the reservoir 62 provide a small amount of flow resistance that is sufficient to prevent the mixture of oxygen and atmospheric air flowing out of the atmospheric air inlet port 55 and thus leaking oxygen. The resistance due to the filter 86 and the baffle plate 82 are intentionally low to not significantly limit the peak pressure that the primary blower 64 can deliver.

The overall inspiratory resistance (i.e., what a patient has to inhale against if the system was turned off to entrain ambient air) may be held to be less than six (6) $cmH_2O$ at 30 L/min. The overall inspiratory resistance is the resistance to air flow due to the filter 86 and resistances in the inspiration tube 26 all the way to the patient coupling device 37, which includes the baffle plate 82, the pressure tap 104, the flow sensors 40, 102, the pressure sensor 106, the filter 28 and the one-way valve 100.

Internal regions of the housing 12 are shielded from bacteria and viruses, especially those coming from the patient. The filter 86 at the air inlet port 75 of the reservoir 62, and the filters 28, 44 in the tubing assembly 24 of the patient circuit, prevent bacteria and viruses from entering the reservoir 62, as well as primary blower 64, the inspiration conduit 66, and the air passage 76 within the housing 12.

While unfiltered air may enter the internal region of the housing 12 due to the fan 98 moving air out of the housing 12, unfiltered air in the housing 12 does not enter the passages for inspiration air that reach the patient. The internal components, e.g., primarily the blower and reservoir assembly 61 and associated gas passages 66, 76 within the housing 12 can be configured to not require cleaning and/or sterilization between patients and/or between treatment sessions of a patient because they are protected by filters from bacteria and viruses.

The tubing assembly 24 of the patient circuit can be configured to be disposable after each use. Also, the relatively flat surfaces of the housing 12 are easy to clean, for example, by being wiped with standard hospital cleaning agents. Thus, the process of readying the ventilator 10 from one use to the next may primarily comprise removing the prior tubing assembly 24 and installing a new tubing assembly 24.

Further, the tubing 26, 32, of the tubing assembly 24 may be long, e.g. five feet or 2.5 meters, or greater, which may allow the patient to be separated from the ventilator housing 12 by a sufficient distance to maintain social distancing between the patient and the health care provider operating the ventilator 10. This social distancing reduces the risk of transmitting bacteria and viruses between the patient and the health care provider.

The controller 108 in the housing 12 controls the blowers, valves, solenoids, user display, monitors the sensors of the ventilator 10 and receives inputs from the user input of the user interface 16 (e.g., positioned on the front panel 14 of the housing 12) and/or via a wireless controller. Power for the controller 108, blowers and other electrical components of the ventilator 10 can be provided by the external power source 51, such as a low voltage DC power supply. A capacitor 120 (FIG. 6) can be configured to provide emergency power for a short period, such as a few minutes, to operate alarms or perform other functions after a loss of external electrical power for the ventilator.

The power consumption of the ventilator 10 may be low, such as less than less than 50 watts. A ventilator 10 has been manufactured and tested by the applicant which uses as little as 20 watts at nominal operation and a maximum of 50 watts at peak power consumption with a mean airway pressure of 28 $cmH_2O$. A ventilator 10 with low power consumption, such as below 80 Watts, 60 Watts and/or no greater than 50 Watts at peak power consumption and with a low nominal operation, such as below 30 Watts or no more than 20 Watts, is advantageous because the ventilator 10 may be operated for hours, such as seven hours, solely on the electrical power stored in the battery 53, which may be a back-up battery.

The ventilator 10 may have component(s) configured to operate with low power consumption, such as the controller 108 with a single low power consumption processor and a low power consumption display, e.g. a liquid crystal display; and blowers to (e.g., secondary blower 128) pump inspiration gases to the patient and control the positive end-expiratory pressure (PEEP) pressure. Further, the oxygen supply may provide $O_2$ at a relatively low pressure and/or low rate, e.g, 15 L/min, into a reservoir 62 and/or the primary blower 64 and can be continuously open to atmospheric air. This assembly 61 of the reservoir 62 and the primary blower 64 provides a low power and simple means to mix oxygen and atmospheric air that provides a stable gas mixture to the patient. Further, the primary blower 64 may have a maximum pressure below a pressure that would harm the lungs of a patient. For example, the maximum inspiration pressure may be no more than 50 $cmH_2O$ or 40 $cmH_2O$. Limiting the maximum inspiration pressure from the primary blower 64 to a safe pressure for inspiration avoids any need for pressure relief valves and monitoring circuits to avoid an overpressure condition.

A primary control function of the ventilator 10 is volume delivery of mixed gases to the patient at defined parameters such as mixed gas volume or inspiratory pressure, inspiratory time and breath rate. The defined parameters may be set by manual inputs to the user interface 16 of the ventilator 10. The control functions may include controlling: mixed gas delivered volume, a mechanical valve activated by positive end-expiratory pressure (PEEP), the breath rate, the inspiratory time, triggering of inspiration and exhalation flows, and watchdog control functions. The monitor functions may include monitoring: flow sensors 102 at the primary blower 64 and at or near the patient; electrical current or power to the motor and system; angular position of the motor and impeller; timing of breath, e.g., inspiration and exhalation; voltage levels in the electrical circuits of the ventilator; pressure at the inspiration port 18; and pressure at the exhalation port 20.

FIG. 7 is a schematic diagram of the pneumatic and electronic components of the ventilator 10. Atmospheric air enters atmospheric air inlet port 55, passes through filter 86 and enters the internal chamber of the reservoir 62. Pure oxygen from oxygen source 60 enters the inner oxygen inlet port 68 (e.g., low flow port) and flows into the reservoir 62 where the oxygen mixes with atmospheric air. The filter 86 may be a viral and/or bacterial particulate filter. Sounds (e.g., noise) emanating from the primary blower 64 are muffled by the baffle plate 82 in the reservoir 62 and by the filter 86.

The volume of the reservoir 62 can be at least two liters, or in a range of 2.3 to 2.8 liters or 2.4 liters. The volume of the internal chamber of the reservoir 62 is substantially greater than the volume of a typical breath, which is typically a tidal volume of two liters. Because the internal chamber of the reservoir 62 has a volume of at least two liters, and preferably in a range of two to three liters, two to four liters, or two to five liters, the reservoir 62 functions as a gas reservoir of a mixture of oxygen and atmospheric air. The reservoir 62 is not depleted during the inspiration phase during which the primary blower 64 is pumping a maximum flow of mixed gas to the patient.

The oxygen level in the internal chamber in the reservoir 62 is relatively stable because of the relatively large volume of the internal chamber. Also, the rate of oxygen entering the reservoir 62 remains relatively constant, but can be subject to adjustment by a user of the ventilator. During the inspiration phase, the suction due to the primary blower 64 pulls atmospheric air into the reservoir 62 at a flow rate greater than during the exhalation phase when the primary blower 64 is pumping at a reduced rate. During the inspiration phase the oxygen level in the reservoir chamber 62 may drop slightly due to the higher flow of atmospheric air. Conversely, during the exhalation phase the oxygen level in the chamber of the reservoir 62 may rise slightly due to a reduced flow of atmospheric air entering the chamber. The volume of the internal chamber of the reservoir 62 is sufficient to moderate the level of oxygen to relatively stable level(s).

The primary blower 64 is located in the reservoir 62 and draws gas from the reservoir 62 consisting of a mix of atmospheric air and oxygen. The primary blower 64 includes a centrifugal impeller enclosed in a housing. A brushless DC blower motor in the primary blower 64 may drive the impeller. Hall sensors in the primary blower 64 may monitor the motor or impeller position and generate data indicating the actual rotational speed of the impeller. This data can be processed by a motor controller (or motor control board) 124 and used as feedback to commutate the phasing of the motor and control the speed of the impeller, pressure at the output of the primary blower air outlet 78 and/or the flow rate at the primary blower air outlet 78. Using a blower to pressurize the inspiratory gas eliminates the need for an external supply of compressed air and limits the maximum pressure of the gas reaching the patient.

The primary blower air outlet 78 is coupled to the inspiration air conduit 66. The inspiration air conduit 66 may include the pressure tap 104, the first pressure sensor 106, the one-way-valve 100 and the flow sensor 102. The inspiration air conduit 66 has an outlet at the inspiration port 18 on the front panel 14 of the housing 12 of the ventilator 10. The inspiration port 18 connects to the inspiration tube 26 and/or the filter 28 as described above. Similarly, the exhalation tube 32 and/or the filter 44 connects to the air exhalation port 20.

Exhaled air from the patient passes through the exhalation tube 32, the air exhalation port 20 and enters the exhalation conduit 114 in the housing 12. The exhalation conduit 114 includes a second pressure sensor 116 and the exhalation valve 118. Exhaled air passes through the exhalation conduit 114, while the exhalation valve 118 is open, and is exhausted from the exhalation exhaust 22.

The controller 108 may include an oxygen control board 121, a main controller (or main control board) 126, and the motor controller (or motor control board) 124. The controller 108 generates a motor control signal using feedback from a sensor (as described herein) monitoring the speed of the motor of primary blower 64 to correct any difference between a desired speed of the motor and the actual speed as detected by the sensor. The motor speed may be calculated to achieve a desired pressure of mixed gases pumped from the primary blower 64. The controller 108 may include an algorithm(s) that correlates the motor speed and pressure to the volume per period, e.g., cubic centimeters per minute, of mixed gases that are pumped. The actual volume of delivered gas may be calculated from integrating the delivered volume with the airway flow sensor 40. The algorithm may be a simple equation and/or a look-up chart that relates motor speed to volume per period, and the algorithm may be configured to make adjustments for ambient temperature and altitude with respect to sea level of the ventilator 10. The motor control signal may set a desired revolutions per minute (RPM) level for the blower motor. In addition to the speed, the motor control signal determines the inspiration period.

Electrical power from the external power source 51 or the battery 53 may be initially received by the power management board 122 and distributed to the motor control board 124, the main control board 126, and the oxygen control board 121. The pressure sensors 106 and 116, and the flow sensors 40 and 102 send data via wires to the main control board 126. The primary blower 64 and a secondary blower 128 communicate with the motor control board 124 and may also communicate with the main control board 126. The motor control board 124 sends commands to the primary blower 64 and the secondary blower 128 to control the speed and torque of the respective blowers. The motor control board 124 may also control a first switch and/or valve, switch valve 130, such as a solenoid valve and/or other electrically activatable valve ("solenoid valve" herein). The switch valve 130 is connected to the output of the secondary blower 128. The secondary blower 128 controls the PEEP (Positive End Expiratory Pressure) pilot pressure which is used to control exhalation pressure during an exhalation phase of the breathing cycle. The PEEP pilot pressure may be in a range of 0 to 15 cmH$_2$O or 0 to 10 cmH$_2$O. This PEEP pilot pressure is multiplied by the area ratio of the exhalation valve to determine the actual PEEP delivered. This pressure is similar to the pressure generated by the secondary blower 128 and used to control the exhalation valve 118 during the exhalation phase.

The user interface 16 allows a health care professional to input settings for a ventilation treatment, such as; inspiratory pressure; tidal volume, e.g., the volume of mixed gases to be delivered to a patient; the inspiratory time; inspiratory and/or expiratory trigger sensitivity; the breathing rate, e.g., breaths per minute (BPM); and the trigger sensitivity, e.g., the flow which triggers the ventilator to switch from inspiration to exhalation. The input settings can be loaded into memory of the controller 108, such as a memory on the main control board 126.

The user interface may include a hand-held user interface device (not shown), e.g., a smart phone with a software application to communicate wirelessly with the controller 108 to transmit input settings and receive information from the ventilator 10 on the ventilation treatment of the patient, such as rate of breathing, alarms issued by the ventilator 10, inspiration and exhalation volumes, inspiratory and expiratory pressures, and/or system parameters, such as motor current and position and/or voltage levels in the ventilator 10. The hand-held user interface device allows the operator, e.g., a nurse or other health care professional to monitor the patient and the ventilator 10 away from the patient, which is especially useful if the patient is isolated due to a virus infection.

The controller 108 and/or an oxygen control board 121 controls a second switch or valve 134, which in turn regulates oxygen flow through the conduit 74 (which may include a one-way valve 135) extending from the outer oxygen inlet port 58 on the rear panel 48 of the housing 12, and the inner oxygen inlet port 68 on the sidewall 69 of the reservoir 62. The second switch or valve 134 may be a solenoid valve and/or other electrically activatable valve ("solenoid valve" herein). The second switch or valve 134 is controlled by an oxygen control board 121 (which is connected to the main control board 126) to open and close the flow of oxygen based on a repeating duty cycle. The duty cycle determines the portion of a cycle that the second switch or valve 134 opens the oxygen flow into the reservoir 62. This opening of the second switch or valve 134 may be initiated at the start of inspiration and may terminate during or after inspiration or at some point during exhalation. In the case of 100% O$_2$, the second switch or valve 134 may be powered on continuously during ventilation. The main control board 126 includes a processor with memory storing instructions and data, such as an algorithm and/or a look-up table. The look-up table or calculated algorithm correlates oxygen levels of the gas mixture in the reservoir 62, the delivered minute ventilation measured by the internal flow sensor 102, the user desired FiO$_2$, and the user set O$_2$ flow rate to the second switch or valve 134 duty cycle that opens the conduit 74 to oxygen flow and/or the portion of the duty cycle that the second switch or valve 134 closes the conduit 74. A user inputs a desired oxygen level, such as between 21% to 30% FiO$_2$ or higher levels of FiO$_2$. The processor on the main control board 126 calculates the duty cycle corresponding to the selected oxygen level such as by using the stored look-up table or by performing a calculation. The user can be requested to set the external flow meter to a default of 15 standard liters per minute (SLPM). This setting would allow the duty cycle to account for variations in minute ventilation and keep the desired O$_2$ level constant in situations where the patient's minute ventilation is varied, for example, as shown in the following equations.

$$\text{DesiredExternalO}_2\text{FlowRate} = \text{DelMinVentilation} * (\%\text{O}_2 - 21)/79 \quad (1)$$

$$\text{DutyCycle} = \text{DesiredExternalO}_2\text{FlowRate} / \text{ActualExternalO}_2\text{FlowRate} \quad (2)$$

where: DesiredExternalO$_2$FlowRate is the flow rate measured in SLPM that is required to achieve the set % O$_2$. DelMin Ventilation is the minute ventilation measured in SLPM delivered by the blower to the patient circuit. % O$_2$ is the user set FiO$_2$ in %. DutyCycle is the % time on for the second switch or valve 134 to achieve the desired % O$_2$.

The frequency of the duty cycle can be set based upon several parameters such as, for example, the ventilator breath rate, the tidal volume, the minute ventilation and the acceptable % O$_2$ ripple in delivery. It should be understood that in standard use, there is less O$_2$ ripple for higher solenoid frequencies. However, higher frequencies can lead to solenoid and/or other valve portion wear out and associated increased power consumption. Thus, the valve-activation frequency may be set to a level of at most 2 Hz and/or at least 0.03 Hz. Knowing the selected duty cycle, the main control board 126 controls the second switch or valve 134 to open and close according to the selected duty cycle at the desired frequency. The duty cycle is repeated by the main control board 126 during the ventilation treatment of patient. The duty cycle may have a cycle time of a few hundred milliseconds to 60 seconds, such as at least 0.5 seconds and/or at most 15 seconds.

Figure 8A:
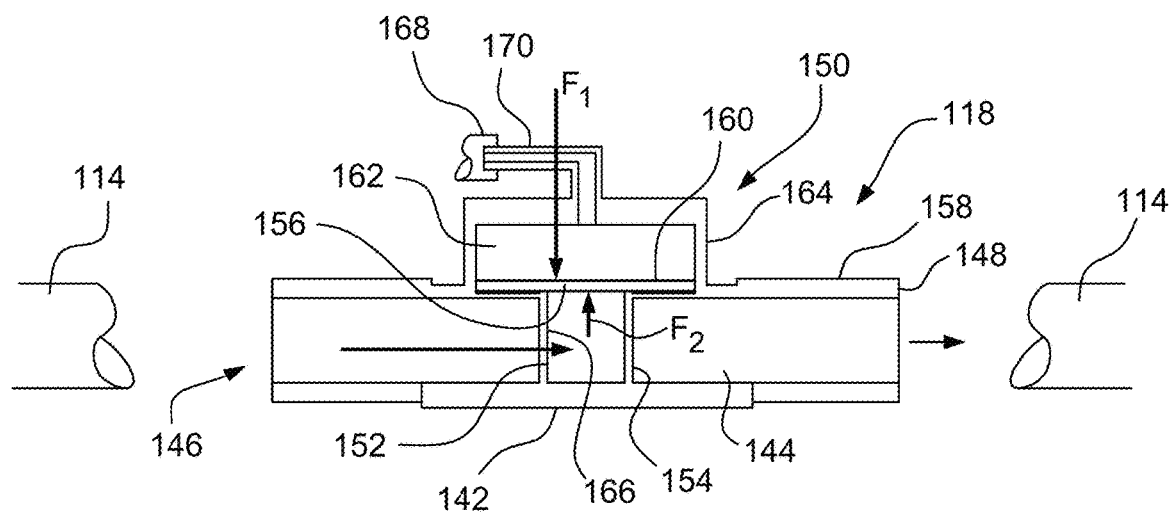
FIGS. 8(A) and 8(B) are side views of a cross section of an exhalation valve in the ventilator.
Figure 8B:
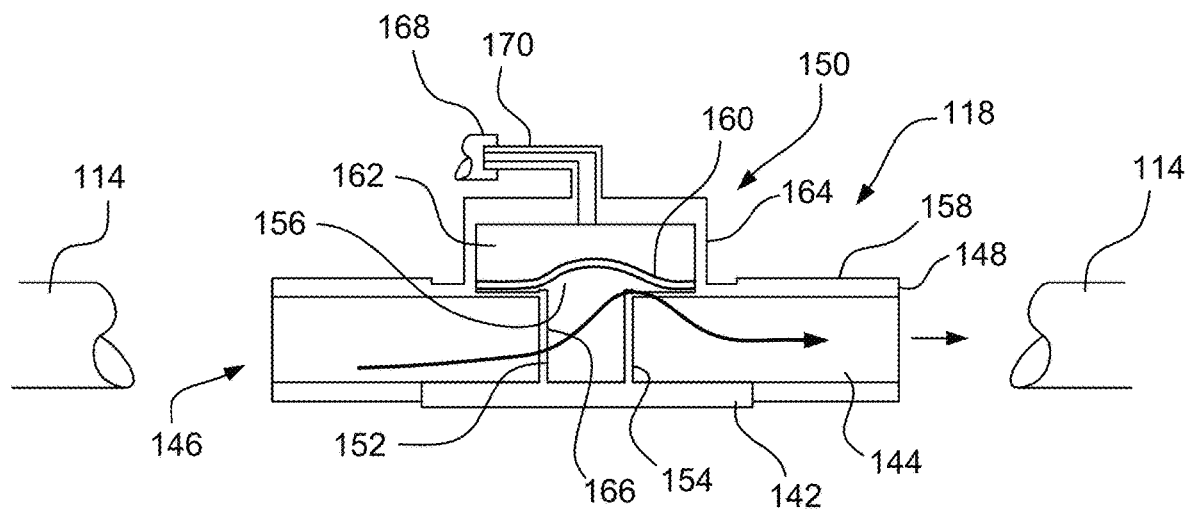

A pressure relief line 136 provides a means for discharging gas from the primary blower 64 to atmosphere during the exhalation phase. The pressure relief line 136 is a passage that branches off of the inspiration air conduit 66 and discharges to atmosphere. The pressure relief line 136 has an inlet connected to the inspiration air conduit 66 near the primary blower outlet 78 and an outlet at one of the panels of the housing 12 (FIG. 7). Alternatively the pressure relief line 136 may be tied to the flow passage 144 (FIGS. 8A and 8B). A pressure relief valve 138 in the pressure relief line 136 allows gas in the inspiration air conduit 66 to be discharged to atmosphere (or into the flow passage 144).

During normal operation, the primary blower 64 continues to draw gas from the reservoir 62 while the patient's respiration is in the exhalation phase. The primary blower 64 need not stop during the exhalation phase and may be kept at a pressure just below PEEP. This has the advantage of preventing unnecessary leakage through the PEEP valve which would increase the O2 losses which are limited in a low flow system. Keeping the primary blower 64 running at a lower speed and hence pressure ensures that a mixture of oxygen and atmospheric air is pumped into the inspiration tube 26 and is ready to quickly flow to the patient at the start of the next inspiration phase.

Providing the pressure relief line 136 with the pressure relief valve 138 also has the advantage of allowing the reservoir 62 to be rapidly flushed to obtain the desired oxygen concentration in the air mixture contained within the reservoir 62. Also, the pressure generated by the primary blower 64 provides resistance to the gas being exhaled by the patient, which helps ensure that the patient does not exhale more breath than is desirable and that an adequate amount of air remains in the lungs minimizing atelectasis. Another benefit of continuously operating the primary blower 64 through both the inspiratory and expiratory phases of the patient's breathing cycle is that the primary blower 64 becomes more efficient and consumes less energy because the primary blower 64 does not need to be repeatedly shut down and restarted.

The pressure relief valve 138 may be regulated to control the amount of gas discharged to atmosphere (or into the exhalation conduit 114 at the exhaust 22) from the inspiratory air conduit 66, which in turn allows for more accurate control of the gas pressure in the inspiratory air conduit 66. In particular, if the pressure in the inspiratory air conduit 66 is greater than the desired pressure (e.g., the pressure in the inspiratory air conduit 66 is interfering with the patient's exhalation), the pressure relief valve 138 is adjusted to allow more gas to flow through the pressure relief line 136. Conversely, if the pressure in the inspiratory air conduit 66 is less than desired (e.g., the pressure in the inspiratory air conduit 66 is not enough to prevent the exhalation gas from infiltrating the primary blower 64) the pressure relief valve 138 is adjusted to restrict the flow of gas through the pressure relief line 136. Although FIG. 7 shows two locations for the exhaust 22, the two exhausts 22 can be combined into one exhaust 22 (as is the case when the pressure relief line discharges into the exhalation conduit 114 at the exhaust 22).

Figure 7A:
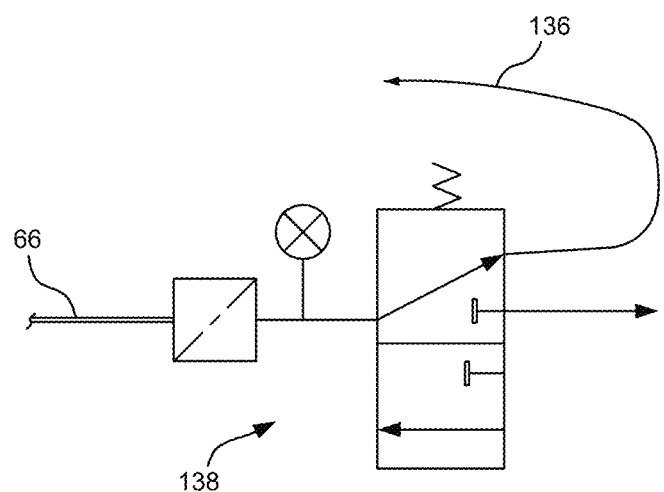
FIG. 7A is a schematic diagram of a 3/2 valve of the ventilator.

It is contemplated that the pressure relief valve 138 may be a one-way valve and may be configured to only open when the pressure difference across the pressure relief valve 138 exceeds a threshold level. Alternatively, the pressure relief valve 138 may be a continuous flow 3/2 way valve, such as a 3/2 way valve that includes a pressure sensor (FIG. 7A). As can be seen, the inlet port in the 3/2 way valve may be connected to the inspiratory air conduit 66, while a first outlet port may be connected to the pressure relief line 136. The second outlet port may be permanently closed. The 3/2 way valve may be used to cyclically control the oxygen flow (e.g., in the form of a duty cycle) between the reservoir 62 and atmosphere (either directly or by way of the exhalation flow passage 144). When the gas in the reservoir 62 is directed to atmosphere, the pressure relief valve 138 limits the gas pressure in the exhalation conduit 114, which can reach as much as 50 psi (or greater) if the exhalation conduit 114 becomes occluded. Thus, the pressure relief valve 138 can help avoid high pressures that could exceed safety limits while at the same time allowing for the continuous flow of oxygen and atmospheric air.

It is further contemplated that the main control board 126 may control the pressure relief valve 138 by way of a solenoid 140. In particular, the main control board 126 may output signals to the solenoid 140 based on input from the flow sensor 102, the pressure sensor 106, and/or the pressure sensor 116 to regulate the pressure relief valve 138 and control the flow of gas through the pressure relief line 136.

The pressure relief line 136 and the pressure relief valve 138 may also provide a second flow path for exhaled gas when there is a blockage in the exhalation tube 32 or exhalation conduit 114 (e.g., debris or a kink in the tubing) to prevent a buildup of exhaled gases in the ventilator 10. A blockage in the exhalation tube 32 or exhalation conduit 114 will result in a significant pressure difference between the inspiration tube 26 (and/or the inspiration air conduit 66) and the exhalation tube 32 (and/or the exhalation conduit 114).

The pressure relief valve 138 is configured to open in response to a substantial pressure difference between at least part of the inhalation passage and at least part of the exhalation passage (the inhalation passage comprising at least the inspiratory air conduit 66 and the inspiratory tube 26 and the exhalation passage comprising at least the exhalation conduit 114 and the exhalation tube 32). The pressure difference sufficient to open the pressure relief valve 138 may be in a range of 3 to 5 cmH$_2$O or 4 to 5 cmH$_2$O. This pressure is slightly below the pressure generated by the secondary blower 128 and is used to control the exhalation valve 118 during the exhalation phase.

The main control board 126 may be configured, e.g., programmed, to operate the primary blower 64 in a "blower back up" mode in the event of a failure of one or more of the flow and/or pressure sensors. During normal operation, these sensors generate signals processed by the main control board 126 to determine the pressure of gases being pumped into the exhalation passage by the primary blower 64. The main control board 126 may be configured to detect a sensor failure (e.g., failure of one or more sensors, such as those described herein) and respond to the sensor failure by operating the primary blower 64 at predefined rotational speeds (RPM) that correspond to the desired inspiratory and expiratory pressure levels. The processor and memory in the main control board 126 execute stored instructions that cause the main control board 126 to detect a sensor failure and respond to such a failure by operating the primary blower 64 in a "blower backup" mode. While in the "blower backup" mode, the main control board 126 may determine a desired pressure of the gas to be pumped by the primary blower 64 based on, for example, a look-up table stored in memory or the existing user setting at a designated breath rate. The look-up table correlates pressure for inhalation to a rotational speed for the primary blower 64. The desired pressure for inhalation gases may be input by a user or selected by the main control board 126 based on inputs such as height and predicted body weight of the patient. Knowing the desired inhalation gas pressure the main control board 126 uses the look-up table to select a primary blower speed corresponding to the desired pressure. The main control board 126 then operates the primary blower 64 at the selected blower speed to achieve the desired inhalation gas pressure. While the "blower backup" mode does not have the benefit of feedback from sensors, this mode will provide inhalation gas at a pressure that is at or reasonably close to the desired inhalation gas pressure. It is also a better response than simply ceasing ventilation. During such an episode a high priority alarm could be annunciated bringing the user's attention to the issue and allowing them time to resolve the issue. During such occurrences in the ICU (intensive care unit), clinicians often resort to a manual resuscitation bag which is essentially the equivalent of the proposed design with the added advantage that there is no delay in the response and that the patient is still ventilated. It is contemplated that the oxygen control board 121, the power management board 122, the motor control board 124, and the main control board 126 may all be different regions of the same control board, may be two or more separate components, and/or may be located in the same region of the ventilator.

FIGS. 8A and 8B show the exhalation valve 118 in schematic diagrams that show a side view of a cross section of the valve. The exhalation valve 118 may have a housing 142 including an exhalation flow passage 144 that is coupled to and in fluid communication with the exhalation conduit 114. An inlet 146 of the exhalation flow passage 144 is connected to the exhalation conduit 114 to receive exhalation air ($Q_{exh}$), and an outlet 148 is coupled to the exhalation conduit 114 to discharge exhalation air into the exhalation conduit 114.

Within the housing 142 is a valve portion 150 that, when closed (FIG. 8A), blocks air flow through the exhalation flow passage 144 and, when open (FIG. 8B), allows air to pass through the exhalation flow passage 144. The valve portion 150 may include a first wall (or annular wall) 152, e.g., an annular disc, and a second wall 154, e.g., a circular disc. The second wall 154 is downstream of the first wall 152. Between the walls 152, 154 is an opening 156 in a sidewall 158 of the exhalation flow passage 144. The opening 156 is selectively opened and closed by a selecting element: for example the opening 156 in FIGS. 8A and 8B is covered by a diaphragm (or selecting element) 160, which may be a circular disc or strip of a deformable material. The diaphragm 160 is between the opening 156 and a chamber 162 within a side housing 164 of the housing 142 of the exhalation valve 118. As shown in FIG. 8A, when the diaphragm 160 seats on the opening 156, the diaphragm 160 closes the valve portion 150 and blocks airflow through the exhalation flow passage 144. When the diaphragm 160 bows away from the opening 156, the valve portion 150 opens and air ($Q_{exh}$) flows through an opening 166 in the first wall 152, the gap between the walls 152, 154, between the diaphragm 160 and a top edge of the second wall 154 and through the exhalation flow passage 144 to the outlet 148 of the exhalation valve 118.

The diaphragm 160 moves between a sealing position (FIG. 8A) which closes the opening 156 and a bowed position (FIG. 8B) which opens a gap between the opening 156 and the diaphragm 160. The diaphragm 160 moves between the sealing position and the bowed position based on a gas pressure difference between the exhalation flow passage 144 and the chamber 162. Chamber 162 has an inlet 168 that is in fluid communication with a tube 170 which extends between the inlet 168 and the switch valve 130. The switch valve 130 may be a solenoid valve that pressurizes the air in tube 170 and the chamber 162 with outlet air from the primary blower 64 or outlet air from the secondary blower 128. As the diaphragm 160 is hermetically coupled to side housing 164, the diaphragm 160 hermetically separates the air chamber 162 from the exhalation flow passage 144, such that pressure in the chamber 162 may be controlled to adjust the pressure in the chamber 162 that provides a force biasing the diaphragm 160 against the pressure in the valve portion 150 which is substantially the pressure of the exhalation gas flowing through the exhalation valve 118.

The diaphragm 160 has a first surface exposed to the chamber 162 and a second surface, opposite to the first, exposed to the opening 156 and the exhalation flow passage 144. The gas force F1 acting on the first surface of the diaphragm 160 is the pressure in the chamber 162 times the area of the first area. Similarly, the gas force F2 acting on the second surface of the diaphragm 160 is the pressure in the exhalation flow passage 144 times the area of the opening 156. The diaphragm 160 is in the closed position when the force F1 is greater than F2 and in the bowed, open position when force F2 is greater than F1. The area of the first surface may be greater than the area of the second surface such as by a factor of two (2).

Having the area of the first surface greater than the area of the second surface allows relatively low pressure air flow from the primary blower 64 and the secondary blower 128 to be used to control the position of the diaphragm 160 and thereby open and close the exhalation valve 118. The primary blower 64 and the secondary blower 128 close the exhalation valve 118 by generating a pressure which when multiplied by the ratio of the first and second areas of the diaphragm 160 is greater than the exhalation gas pressure in the exhalation flow passage 144.

The exhalation valve 118 may be mounted within the housing of the ventilator 10. Alternatively, the exhalation valve 118 may be integrated in the tubing assembly 24 or be a separate component that is releasably attached to the housing 12, such as at the exhalation exhaust port 22.

The exhalation valve 118 may be shielded from viruses and bacteria in an exhaled breath. In particular, the exhaust gas passing through the exhalation valve 118 can be cleaned by filter 44. The exhalation valve 118 is not contaminated by viruses or bacteria exhaled by the patient. Similarly, other components within the housing 12 of the ventilator 10 exposed to inspiration or exhalation gases are shielded from bacteria and viruses due to these filters. In particular, the blower and reservoir assembly 61 and inspiration air conduit 66 are protected by the filter 86 at the atmospheric air inlet port 55, and the exhalation conduit 114 is protected by the filter 44.

Figure 9:
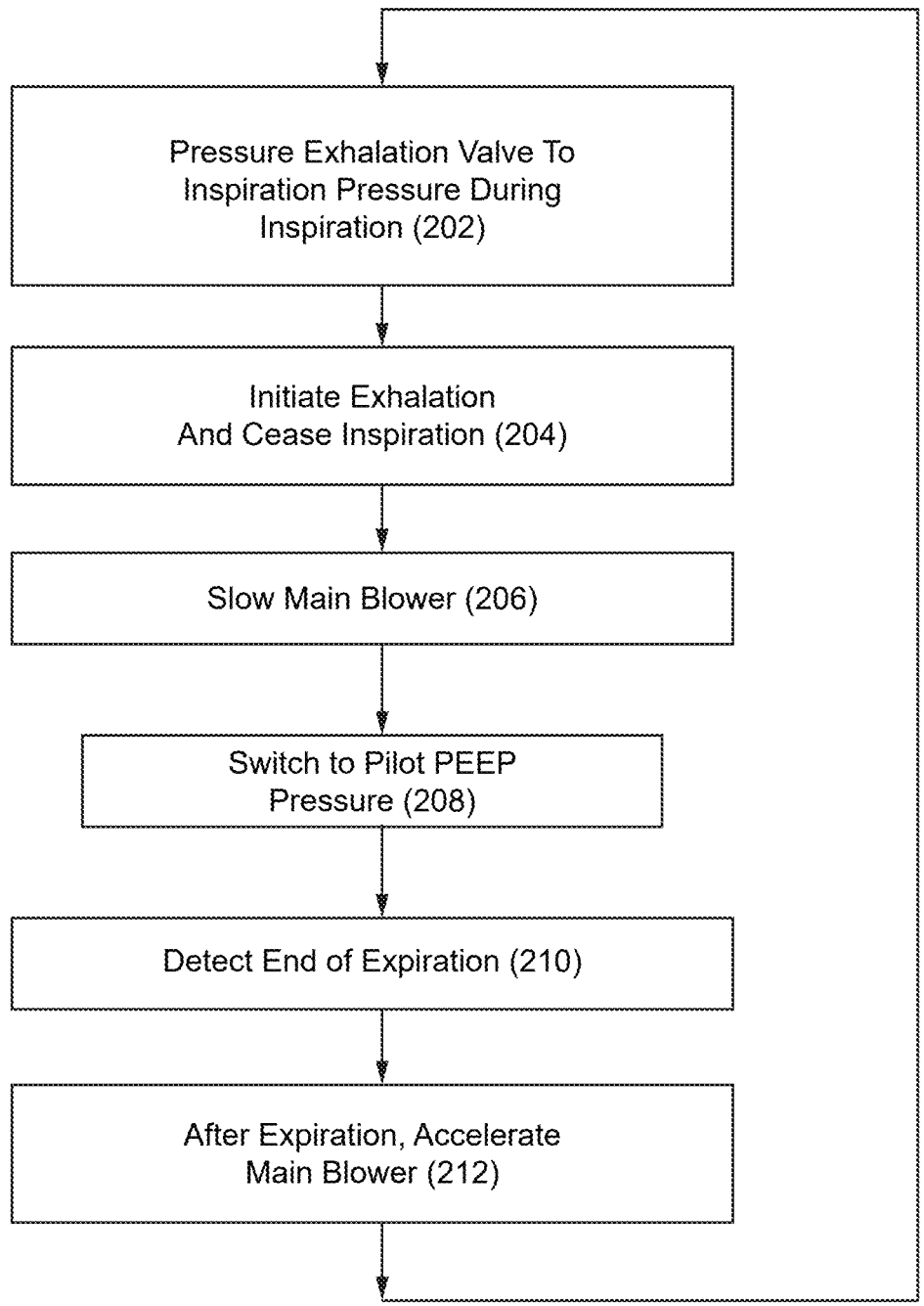
FIG. 9 is a flow chart showing the operation of the exhalation valve and switching between inspiration and exhalation phases of the ventilator.

FIG. 9 is a flow chart showing the control of the exhalation valve 118. The exhalation valve 118 is closed while the ventilator 10 pumps a mixture of atmospheric air and oxygen to the patient (the inspiration phase) and at the end of the exhalation phase when the pressure of the air exhaled by the patient falls below the PEEP expiratory pressure. The opening and closing of the exhalation valve 118 are controlled by the pressure, e.g., the pilot pressure, in the chamber 162 of the valve.

During inspiration (step 202), the pilot pressure in the chamber 162 equals the inspiration pressure. The inspiration pressure is the pressure at the outlet of the primary blower 64 while the primary blower 64 is operating to pump inspiration gases into the inspiration tube 26, through the Y-junction coupling 30 and to the patient via the connection tube 34. Because the passages in the Y-junction coupling 30 and the connection tube 34 may contain gas at a pressure at or near, e.g., within 95%, the inspiration pressure, the pressure in the exhalation tube 32 and in the exhalation flow passage 144 in the exhalation valve 118 are also at the inspiration pressure. Thus, pressure in the exhalation flow passage 144 and the pilot pressure chamber 162 are at substantially the same inspiration pressure. Due to the greater area of the first surface of the side of the diaphragm 160 exposed to the pilot pressure chamber 162 than the second surface of the side of the diaphragm 160 exposed to the exhalation flow passage 144, the diaphragm 160 is forced against the opening 156 and closes the exhalation valve 118 during the inspiration phase. Closing the exhalation valve 118 during inspiration prevents inspiration gases from leaking out the exhalation tube 32 and assists in forcing the inspiration gases into the patient.

In step 204, the controller 108, e.g., main control board 126, determines that an inspiration phase is completed and a new exhalation phase is to start. The controller 108 switches between inspiration and exhalation phases based on control algorithms that may include regular cyclical inspiration and exhalation periods, based on the detection by the flow sensor 40 of a patient-initiated inhalation or exhalation of a breath, or based on other parameters for determining when to initiate inspiration and exhalation.

When the controller 108 determines that an exhalation phase is to be initiated, the rotational speed of the impeller in the primary blower 64 is slowed (step 206). The impeller of the primary blower 64 is slowed to reduce the loss of oxygen from the blower and reservoir assembly 61 during an exhalation phase. Oxygen continuously flows into the reservoir 62 from the source of oxygen ($O_2$) via ports 58, 68. Slowing the impeller in the primary blower 64 reduces the pressure drop in the reservoir 62 due to the suction of the primary blower 64 which slows the rate of oxygen into the reservoir 62 and the rate of atmospheric air entering through inlet port 55 and passing through filter 86. The primary blower 64 need not stop during the exhalation phase and may be kept at a pressure just below PEEP. This continued operation of the primary blower 64 has the advantage of preventing unnecessary leakage through the PEEP valve which would increase the O2 losses which are limited in a low flow system. Keeping the primary blower 64 running at a lower speed and corresponding lower pressure ensures that a mixture of oxygen and atmospheric air is pumped into the inspiration tube 26 and is ready to quickly flow to the patient at the start of the next inspiration phase.

When the controller 108 determines that an exhalation phase is to be initiated (step 208), the controller 108 actuates the switch valve 130 to direct the output of the secondary blower 128 to the tube 170 and the inlet 168 of the pilot pressure chamber 162 of the exhalation valve 118. The switch valve 130 also closes the tube 170 from the primary blower 64 when pressure is being provided by the secondary blower 128 to the chamber 162. During exhalation, the pilot pressure is set to the desired PEEP pilot pressure divided by the area ratio of the diaphragm 160 to ensure that the expiratory pressure in the exhalation conduit 114 and exhalation tube 32 remains above PEEP. Thus, the patient's exhalation pressure has to exceed the desired PEEP pilot pressure for the exhalation conduit 114 to remain open. The area ratio of the diaphragm 160 is the ratio of the first surface area of the diaphragm 160 exposed to chamber 162 and the second surface area exposed to the opening 156 to the exhalation conduit 114. Maintaining the pressure in the exhalation conduit 114 and tube 32 at PEEP pressure ensures that the patient does not exhale more breath than is desirable and that an adequate amount of air remains in the lungs minimizing atelectasis.

The secondary blower 128 pressurizes the pilot pressure chamber 162 of the exhalation valve 118 during the entirety of the exhalation phase. During exhalation, the patient exhales at a pressure above the desired PEEP pressure such that the exhaled air flows from the patient through the exhalation tube 32, the exhalation conduit 114, the exhalation valve 118, the exhalation exhaust 22 and out to atmosphere.

In step 210, the end of exhalation may be detected by the patient initiating a new inhaled breath, such as by the flow sensor 40 detecting air flowing into the patient rather than out. Alternatively, data from the pressure sensor 116 in the exhalation conduit 114 may be analyzed by the controller 108 to determine the end of exhalation, such as by detecting an exhalation air pressure at or below PEEP. The end of exhalation may also be determined by the end of a certain exhalation period.

The controller 108 determines the end of exhalation and beginning of inspiration. Exhalation and inspiration may be the two operating phases of the ventilator 10. Thus, the end of exhalation is the beginning of inspiration and vice versa. The use of a plateau pressure extends the inspiratory phase without gas delivery.

In step 212, the impeller speed of the primary blower 64 is accelerated to cause the primary blower 64 to output a mixture of atmospheric air and oxygen at a desired inspiration air pressure. This mixture is pumped through the inspiration air conduit 66, inspiration tube 26 and to the patient. The controller 108 controls the motor speed and accelerates the primary blower 64 to a speed to produce the desired inspiration pressure and/or air flow.

In response to the detection of the end of exhalation (step 210), the controller 108 restarts the steps shown in FIG. 9 and at the commencement of an inspiration phase, actuates the switch valve 130 to switch the gas pressure from PEEP pressure produced by the secondary blower 128 to the inspiration pressure produced by the primary blower 64, in step 202. The pressure flows from the primary blower 64, through the switch valve 130, through the tube 170 and to the pilot pressure chamber 162 of the exhalation valve 118. Pressurizing the chamber 162 to the inspiration pressure closes the exhalation valve 118 and prevents airflow through the exhalation tube 32 during the inspiration phase.

The ventilator 10 may be configured as an inexpensive ventilator that can be quickly brought on line after being in storage for years. The ventilator 10 may be used when there is a surge of patients needing ventilation, such as during a pandemic or other epidemic (e.g., the COVID-19 pandemic). The ventilator 10 may be used to ventilate patients who have less severe conditions, which tend to be a majority of patients during surge conditions. To keep the cost low and to provide for long term storage, the ventilator 10 may be designed to provide patients with basic ventilation and not have the ability to provide sophisticated ventilation functions required of some patients in an intensive care unit (ICU). Thus, the ventilator 10 may be used to free-up beds in an ICU by treating patients who need to be ventilated but do not require an ICU bed. The ventilator 10 may have a single, basic mode of mandatory ventilator support which assists to facilitate ease of use and reduction on the burden of highly specialized personnel to operate or can include multiple modes (e.g., mandatory, assist and spontaneous modes) of ventilation. The ventilator 10 is electro-mechanically and pneumatically operated, providing mechanical ventilation using: two blowers 64, 128 to generate air pressure and air flow, wherein the primary blower 64 pumps inspiration gases at a pressure determined by the controller and the secondary blower 128 pumps a pilot pressure to the exhalation valve 118 which closes if the exhalation gas pressure falls below PEEP pressure.

The switch valve 130 switches the pilot pressure applied to the pilot pressure chamber 162 of the exhalation valve 118 between the inspiration pressure from the primary blower 64 and the secondary blower 128 pressure. The pilot pressures are applied to the exhalation valve 118 to hold the exhalation valve 118 closed during inspiration and keep the exhalation valve 118 open during exhalation as long as the exhalation pressure remains above PEEP pressure.

The ventilator 10 may be configured, such as with executable algorithms stored in the controller, to operate in different ventilation modes. The modes are selected by the user, e.g., a health care professional operating the ventilator 10. The modes may include: Pressure Control Ventilation (PCV) mode for which a health care professional may, via the user interface, set: Inspiratory Pressure Target (PI); Inspiratory Time (TI) and/or Breath Rate (f); Pressure Support Ventilation (PSV) mode the health care professional may set: Pressure Support Target ($P_{SUPP}$) and/or Exhalation Sensitivity ($E_{SENS}$); SIMV mode which is a hybrid of PCV and PSV mode in which the user may set: Inspiratory Pressure Target (PI); and Inspiratory Time (TI); Breath Rate (f); Pressure Support Target ($P_{SUPP}$) and Exhalation Sensitivity ($E_{SENS}$).

In addition to the modes of ventilation, the various common settings of the ventilator 10 may be set by the user. These Common Settings may include: Trigger Sensitivity (Lpm or unitless); desired oxygen percent in inspiration gas ($O_2$%); PEEP pressure level; alarm settings; Low Exhaled Tidal Volume; High Respiratory Rate (HRR); Disconnect Limit; Low Inspiratory Pressure Limit; High Pressure Limit and Apnea Limit. These user settable features provide functionality to the ventilator to provide life supporting ventilation to a patient.

Figure 10:
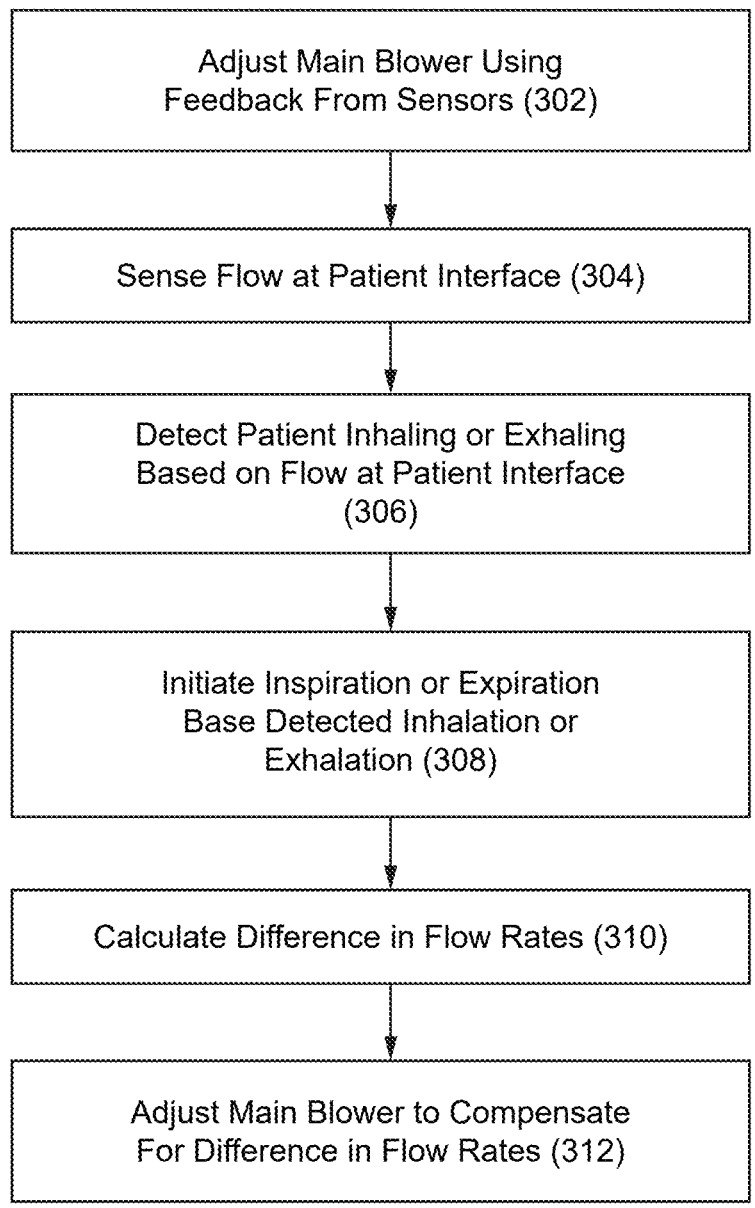
FIG. 10 is a flow chart of a portion of control algorithm for the primary blower.

As shown in the flow chart of FIG. 10, the flow sensor 40 and the first pressure sensor 106 near the primary blower outlet 78 measures pressure and/or flow volume of the gas mixture discharged by the primary blower 64. In step 302, the controller 108 uses the measured pressure and/or flow as feedback to adjust the impeller speed of the primary blower 64 to achieve desired inspiration gas pressure and/or flow volume levels. In step 304, the flow sensor 40 near the patient interface measures the flow direction and/or flow volume being inhaled and exhaled by the patient. In step 306, the controller 108 uses the sensing of flow direction and/or flow measurement from the flow sensor 40 to detect the patient initiating an inhale or exhale of a breath. In step 308, the controller 108 initiates an inspiration phase of the ventilator 10 in response to the patient inhaling and initiates an exhalation phase in response to the patient exhaling.

The controller 108 may adjust the volume or rate of the gas mixture being pumped by the primary blower 64 to account for gas leakage between the primary blower 64 and the patient. In step 310, the controller 108 determines a difference between the flow rate measured by flow sensor 102 at the primary blower outlet 78 and the flow rate measured by flow sensor 40 near the patient. The difference in flow rates is indicative of leakage of the gas mixture. In step 312, the controller 108 adjusts the speed of the impeller of the primary blower 64 or the timing of the inspiration phase to compensate for the difference in the flow rates and thus the gas leakage.

Figure 11:
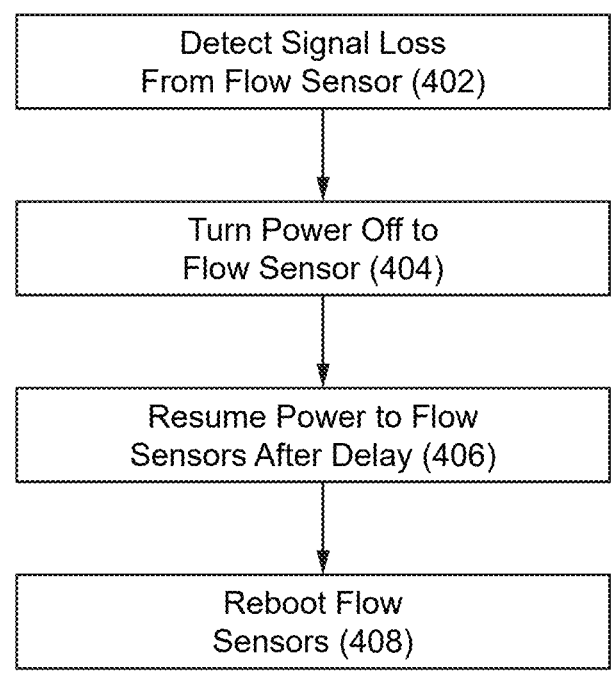
FIG. 11 is a flow chart for resetting the flow control sensors.

FIG. 11 is a flow chart showing a failsafe operation to reset the flow sensors 40, 102. This method can be used for any CMOS interface which facilitates the status determination of a CMOS device. The first and second flow sensors 40, 102 may be subject to a failure mode in which they latchup. Latching is a concern for any devices based on CMOS technology. A latchup of the flow sensor(s) may occur due to a ground bounce during an electrostatic discharge (ESD), such as a nearby lightning strike, or due to electromagnetic interference (EMI) due to a nearby, high-powered medical device. In step 402, the controller 108 detects a latchup condition or other signal loss in either or both of the flow sensors 40, 102. The detection may be the controller 108 sensing a loss of communication signals from one or both of the flow sensors 40, 102. In step 404, the controller 108 responds to a detected latchup by turning off power to either or both the flow sensors 40, 102. In step 406, the controller 108 applies power to either or both of the flow sensors 40, 102 after a certain delay such as a delay of five to ten seconds. In step 408, the flow sensors 40, 102 reboot in response to the resumption of power. The rebooting allows the flow sensors 40, 102 to resume communication with the controller 108 by eliminating the latchup.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means "and/or" (either or both). Furthermore, characteristics or steps which have been described may also be used in combination with other characteristics or steps and in any order unless the disclosure or context suggests otherwise.

The invention claimed is:

1. A ventilator (10), comprising:
   a housing (12);
   a reservoir (62) within the housing (12), wherein the reservoir (62) comprises:
      an internal chamber;
      an air inlet port (55) configured to place in fluid communication the internal chamber with atmospheric air outside the reservoir (62); and an oxygen inlet port (68) configured to place in fluid communication the internal chamber with a source of oxygen;

an oxygen switch valve (134) configured to regulate a flow of oxygen from the source of oxygen to the oxygen inlet port (68);

a primary blower (64) having a gas inlet in fluid communication with the internal chamber of the reservoir (62), and a gas outlet configured to be placed in fluid communication with an inspiration tube (26) external of the housing; and a fan (98) configured to exhaust gasses within the housing (12) to atmospheric air, wherein the internal chamber of the reservoir (62) presents a volume for gas mixing extending at least between the air inlet port (55), the oxygen inlet port (68), and the primary blower gas inlet, and wherein said volume is configured to allow mixing of air entering the reservoir via the air inlet port (55) with oxygen entering the reservoir via the oxygen inlet port (68) before any gas reaches the primary blower gas inlet.

2. The ventilator according to claim 1, further comprising a controller (108) configured to control the oxygen switch valve (134).

3. The ventilator according to claim 2, further comprising an oxygen sensor (110), wherein the controller (108) is configured to regulate the flow of oxygen through the oxygen switch valve (134) based on signals from the oxygen sensor (110).

4. The ventilator according to claim 1, wherein a flowrate of the fan (98) is greater than a flowrate of oxygen into the ventilator (10).

5. The ventilator according to claim 1, wherein the volume of the internal chamber of the reservoir (62) communicates with outside of the reservoir only via the air inlet port (55), the oxygen inlet port (68), and the primary blower gas inlet.

6. The ventilator according to claim 1, wherein the air inlet port (55) is a continuously open port constantly placing in fluid communication the internal chamber with atmospheric air outside the reservoir (62).

7. The ventilator according to claim 1, further comprising an air filter (86) coupled to the air inlet port (55) and configured to filter atmospheric air entering the internal chamber.

8. A ventilator (10), comprising:

a housing (12);

a reservoir (62) within the housing (12), wherein the reservoir (62) comprises:

an internal chamber;

an air inlet port (55) configured to place in fluid communication the internal chamber with atmospheric air outside the reservoir (62); and an oxygen inlet port (68) configured to place in fluid communication the internal chamber with a source of oxygen;

an oxygen switch valve (134) configured to regulate a flow of oxygen from the source of oxygen to the oxygen inlet port (68); and a primary blower (64) having a gas inlet in fluid communication with the internal chamber of the reservoir (62), and a gas outlet configured to be placed in fluid communication with an inspiration tube (26) external of the housing, wherein the internal chamber of the reservoir (62) presents a volume for gas mixing extending at least between the air inlet port (55), the oxygen inlet port (68), and the primary blower gas inlet, wherein said volume is configured to allow mixing of air entering the reservoir via the air inlet port (55) with oxygen entering the reservoir via the oxygen inlet port (68) before any gas reaches the primary blower gas inlet, and wherein the primary blower (64) is located in the reservoir (62) and wherein the gas mixing volume of the internal chamber of the reservoir (62) comprises a volume of the internal chamber of the reservoir not occupied by the primary blower (64).

9. The ventilator according to claim 8, further comprising a fan (98) configured to exhaust gases within the housing (12) to atmospheric air.

10. The ventilator according to claim 9, wherein a flowrate of the fan (98) is greater than a flowrate of oxygen into the ventilator (10).

11. The ventilator according to claim 8, wherein the gas mixing volume of the internal chamber of the reservoir (62) is at least as great as two liters.

12. The ventilator according to claim 8, comprising the inspiration tube (26) connected to the gas outlet of the primary blower (64), and wherein the volume of the internal chamber of the reservoir (62) is at least as great as a volume inside the inspiration tube (26).

13. The ventilator according to claim 8, wherein the volume of the internal chamber of the reservoir (62) communicates with outside of the reservoir only via the air inlet port (55), the oxygen inlet port (68), and the primary blower gas inlet.

14. A ventilator (10), comprising:

a housing (12);

a reservoir (62) within the housing (12), wherein the reservoir (62) comprises:

an internal chamber;

an air inlet port (55) configured to place in fluid communication the internal chamber with atmospheric air outside the reservoir (62); and an oxygen inlet port (68) configured to place in fluid communication the internal chamber with a source of oxygen;

an oxygen switch valve (134) configured to regulate a flow of oxygen from the source of oxygen to the oxygen inlet port (68); and a primary blower (64) having a gas inlet in fluid communication with the internal chamber of the reservoir (62), and a gas outlet configured to be placed in fluid communication with an inspiration tube (26) external of the housing, wherein the internal chamber of the reservoir (62) presents a volume for gas mixing extending at least between the air inlet port (55), the oxygen inlet port (68), and the primary blower gas inlet, wherein said volume is configured to allow mixing of air entering the reservoir via the air inlet port (55) with oxygen entering the reservoir via the oxygen inlet port (68) before any gas reaches the primary blower gas inlet, and wherein the oxygen inlet port (68) is connected through the oxygen switch valve (134) and a conduit (79) to an oxygen inlet (58) on the housing (62) and wherein at least one of the oxygen inlet port (68), the conduit (79), and the oxygen inlet (58) has a flow passage with a cross-sectional area that is substantially smaller than a cross-sectional area of a flow passage at the air inlet port (55) to the reservoir (62).

15. The ventilator according to claim 14, further comprising a controller (108) configured to control the oxygen switch valve (134).

16. The ventilator according to claim 15, further comprising an oxygen sensor (110), wherein the controller (108) is configured to regulate the flow of oxygen through the oxygen switch valve (134) based on signals from the oxygen sensor (110).

17. The ventilator according to claim 14, wherein the gas mixing volume of the internal chamber of the reservoir (62) is at least as great as two liters.

18. The ventilator according to claim 14, wherein the volume of the internal chamber of the reservoir (62) communicates with outside of the reservoir only via the air inlet port (55), the oxygen inlet port (68), and the primary blower gas inlet.

19. The ventilator according to claim 14, wherein the oxygen inlet port (68) is positioned on a sidewall of the reservoir (62) at a distance from the air inlet port (55) and a distance from the gas inlet of the primary blower (64), such that the flow of oxygen through the oxygen inlet port (68) crosses the flow of air through the air inlet port (55) facilitating formation of a gas mixture upstream of the gas inlet of the primary blower (64).

20. The ventilator according to claim 19, wherein the distance of the oxygen inlet port (68) from the air inlet port (55) is comprised of between 70% and 130% of the distance of the same oxygen inlet port (68) to the gas inlet of the primary blower (64).

21. The ventilator according to claim 19, wherein the distance from the oxygen inlet port (68) to the air inlet port (55) is between 80% and 120%, of the distance from the same oxygen inlet port (68) to the gas inlet of the primary blower (64).

22. The ventilator according to claim 14, wherein the cross-sectional area of the flow passage of the oxygen inlet (58) is less than 75% of the cross-sectional area of the flow passage at the air inlet port (55) to the reservoir (62).

23. The ventilator according to claim 14, wherein the cross-sectional area of the flow passage of the oxygen inlet (58) is less than 50% of the cross-sectional area of the flow passage at the air inlet port (55) to the reservoir (62).

24. The ventilator according to claim 14, wherein the cross-sectional area of the flow passage of the oxygen inlet (58) is less than 25% of the cross-sectional area of the flow passage at the air inlet port (55) to the reservoir (62).

25. The ventilator according to claim 14, wherein the cross-sectional area of the flow passage of the oxygen inlet (58) is less than 10% of the cross-sectional area of the flow passage at the air inlet port (55) to the reservoir (62).

26. A ventilator (10), comprising:
a housing (12);
a reservoir (62) within the housing (12), wherein the reservoir (62) comprises:
an internal chamber;
an air inlet port (55) configured to place in fluid communication the internal chamber with atmospheric air outside the reservoir (62); and
an oxygen inlet port (68) configured to place in fluid communication the internal chamber with a source of oxygen;
an oxygen switch valve (134) configured to regulate a flow of oxygen from the source of oxygen to the oxygen inlet port (68);
a primary blower (64) having a gas inlet in fluid communication with the internal chamber of the reservoir (62), and a gas outlet configured to be placed in fluid communication with an inspiration tube (26) external of the housing;
an exhalation port (20) configured to be placed in fluid communication with an exhalation tube (32) receiving exhaled air; and
an exhalation valve (118) that opens or obstructs flow through the exhalation port (20) or through an exhalation conduit (114) connected to the exhalation port (20), depending on whether the ventilator is in an inspiration phase, wherein the exhalation valve (118) is closed, or in an exhalation phase, when the exhalation valve (118) is open,
wherein the internal chamber of the reservoir (62) presents a volume for gas mixing extending at least between the air inlet port (55), the oxygen inlet port (68), and the primary blower gas inlet,
wherein said volume is configured to allow mixing of air entering the reservoir via the air inlet port (55) with oxygen entering the reservoir via the oxygen inlet port (68) before any gas reaches the primary blower gas inlet, and
wherein the exhalation port (20) is connected to the exhalation conduit (114) that directs the exhaled air and other gases to an exhaust port (22) on a front panel of the housing (12), and wherein the exhalation conduit (114) includes the exhalation valve (118).

27. The ventilator according to claim 26, further comprising a controller (108) configured to control the oxygen switch valve (134).

28. The ventilator according to claim 27, further comprising an oxygen sensor (110), wherein the controller (108) is configured to regulate the flow of oxygen through the oxygen switch valve (134) based on signals from the oxygen sensor (110).

29. The ventilator according to claim 26, further comprising a fan (98) configured to exhaust gases within the housing (12) to atmospheric air.

30. The ventilator according to claim 29, wherein a flowrate of the fan (98) is greater than a flowrate of oxygen into the ventilator (10).

31. The ventilator according to claim 26, wherein the exhalation valve (118) comprises:
an exhalation flow passage (144) that has an inlet (146), coupled to and in fluid communication with the exhalation conduit (114) or with the exhalation port (20) to receive exhalation air coming from the exhalation port (20), an outlet (148) to discharge exhalation air, and an opening (156) in a sidewall of the exhalation flow passage (144) allowing fluid communication between the inlet (146) and the outlet (148) of the exhalation flow passage (144), and
a selecting element (160) comprising a surface that is selectively movable between a closed position, in which the selecting element (160) closes the opening (156) in the sidewall of the exhalation flow passage (144) and prevents passage of air through the exhalation flow passage (144) and an open position, in which the selecting element (160) leaves said opening (156) in the sidewall open and allows passage of air through the exhalation flow passage (144).

32. The ventilator according to claim 31, wherein the exhalation valve (118) comprises a valve portion (150) that, when closed, blocks air flow through the exhalation flow passage (144) and, when open, allows air to pass through the exhalation flow passage (144), wherein the valve portion (150) includes:

a first wall (152), and a second wall (154), wherein the second wall (154) is downstream in the exhalation flow passage (144) of the first wall (152), wherein the opening (156) in the sidewall of the exhalation flow passage (144) is located between the first and second walls (152, 154).

33. The ventilator according to claim 32, wherein the exhalation valve (118) comprises a chamber (162), and wherein the selecting element (160) is in the form of a diaphragm and operates between the opening (156) and the chamber (162).

34. The ventilator according to claim 33, wherein the diaphragm (160) in the closed position seats on the opening (156) and closes the valve portion (150) blocking airflow through the exhalation flow passage (144), and in the open position bows away from the opening (156) and opens the valve portion (150) allowing air flow through the exhalation flow passage (144) to the outlet (148).

35. The ventilator according to claim 32, wherein the first wall (152) is in the form of an annular disc, and the second wall (154) is in the form of a circular disc.

36. A ventilator (10), comprising:
a housing (12);
a reservoir (62) within the housing (12), wherein the reservoir (62) comprises:
an internal chamber;
an air inlet port (55) configured to place in fluid communication the internal chamber with atmospheric air outside the reservoir (62); and
an oxygen inlet port (68) configured to place in fluid communication the internal chamber with a source of oxygen;
an oxygen switch valve (134) configured to regulate a flow of oxygen from the source of oxygen to the oxygen inlet port (68);
a primary blower (64) having a gas inlet in fluid communication with the internal chamber of the reservoir (62), and a gas outlet configured to be placed in fluid communication with an inspiration tube (26) external of the housing;
an exhalation port (20) configured to be placed in fluid communication with an exhalation tube (32) receiving exhaled air; and
an exhalation valve (118) that opens or obstructs flow through the exhalation port (20) or through an exhalation conduit (114) connected to the exhalation port (20), depending on whether the ventilator is in an inspiration phase, wherein the exhalation valve (118) is closed, or in an exhalation phase, when the exhalation valve (118) is open, wherein the exhalation valve (118) comprises:
an exhalation flow passage (144) that has an inlet (146), coupled to and in fluid communication with the exhalation conduit (114) or with the exhalation port (20) to receive exhalation air coming from the exhalation port (20), an outlet (148) to discharge exhalation air, and an opening (156) in a sidewall of the exhalation flow passage (144) allowing fluid communication between the inlet (146) and the outlet (148) of the exhalation flow passage (144), and
a selecting element (160) comprising a surface that is selectively movable between a closed position, in which the selecting element (160) closes the opening (156) in the sidewall of the exhalation flow passage (144) and prevents passage of air through the exhalation flow passage (144) and an open position, in which the selecting element (160) leaves said opening (156) in the sidewall open and allows passage of air through the exhalation flow passage (144), wherein the internal chamber of the reservoir (62) presents a volume for gas mixing extending at least between the air inlet port (55), the oxygen inlet port (68), and the primary blower gas inlet, and wherein said volume is configured to allow mixing of air entering the reservoir via the air inlet port (55) with oxygen entering the reservoir via the oxygen inlet port (68) before any gas reaches the primary blower gas inlet.

37. The ventilator according to claim 36, further comprising a controller (108) configured to control the oxygen switch valve (134).

38. The ventilator according to claim 37, further comprising an oxygen sensor (110), wherein the controller (108) is configured to regulate the flow of oxygen through the oxygen switch valve (134) based on signals from the oxygen sensor (110).

39. The ventilator according to claim 36, further comprising a fan (98) configured to exhaust gases within the housing (12) to atmospheric air.

40. The ventilator according to claim 39, wherein a flowrate of the fan (98) is greater than a flowrate of oxygen into the ventilator (10).

41. The ventilator according to claim 36, wherein the exhalation valve (118) comprises a valve portion (150) that, when closed, blocks air flow through the exhalation flow passage (144) and, when open, allows air to pass through the exhalation flow passage (144), wherein the valve portion (150) includes:
a first wall (152), and
a second wall (154), wherein the second wall (154) is downstream in the exhalation flow passage (144) of the first wall (152),
wherein the opening (156) in the sidewall of the exhalation flow passage (144) is located between the first and second walls (152, 154).

42. The ventilator according to claim 41, wherein the exhalation valve (118) comprises a chamber (162), and wherein the selecting element (160) is in the form of a diaphragm and operates between the opening (156) and the chamber (162).

43. The ventilator according to claim 42, wherein the diaphragm (160) in the closed position seats on the opening (156) and closes the valve portion (150) blocking airflow through the exhalation flow passage (144), and in the open position bows away from the opening (156) and opens the valve portion (150) allowing air flow through the exhalation flow passage (144) to the outlet (148).

44. The ventilator according to claim 41, wherein the first wall (152) is in the form of an annular disc, and the second wall (154) is in the form of a circular disc.

45. A ventilator (10), comprising:
a housing (12);
a reservoir (62) within the housing (12), wherein the reservoir (62) comprises:
an internal chamber;
an air inlet port (55) configured to place in fluid communication the internal chamber with atmospheric air outside the reservoir (62); and
an oxygen inlet port (68) configured to place in fluid communication the internal chamber with a source of oxygen;

an oxygen switch valve (134) configured to regulate a flow of oxygen from the source of oxygen to the oxygen inlet port (68);

a primary blower (64) having a gas inlet in fluid communication with the internal chamber of the reservoir (62), and a gas outlet configured to be placed in fluid communication with an inspiration tube (26) external of the housing;

an inspiration conduit (66) that is configured to convey pressurized gas from the primary blower (64) to the inspiration tube (26);

a pressure relief line (136) including an inlet connected to the inspiration conduit (66) and located downstream of the primary blower (64) and an outlet in communication with atmospheric air; and a pressure relief valve (138) within the pressure relief line (136), wherein the internal chamber of the reservoir (62) presents a volume for gas mixing extending at least between the air inlet port (55), the oxygen inlet port (68), and the primary blower gas inlet, wherein said volume is configured to allow mixing of air entering the reservoir via the air inlet port (55) with oxygen entering the reservoir via the oxygen inlet port (68) before any gas reaches the primary blower gas inlet, and wherein the pressure relief valve (138) is configured to open to allow gas to flow through the pressure relief line (136) if a pressure difference across the pressure relief valve (138) exceeds a threshold pressure value, and the pressure relief valve (136) is configured to close the pressure relief line (136) if the pressure difference across the pressure relief valve (138) is lower than the threshold pressure value.

46. The ventilator according to claim 45, further comprising a controller (108) configured to control the oxygen switch valve (134).

47. The ventilator according to claim 46, further comprising an oxygen sensor (110), wherein the controller (108) is configured to regulate the flow of oxygen through the oxygen switch valve (134) based on signals from the oxygen sensor (110).

48. The ventilator according to claim 45, further comprising a fan (98) configured to exhaust gases within the housing (12) to atmospheric air.

49. The ventilator according to claim 48, wherein a flowrate of the fan (98) is greater than a flowrate of oxygen into the ventilator (10).

50. The ventilator according to claim 45, further comprising at least one pressure sensor (106, 116) configured to sense pressure(s) in the inspiration tube (26), and a controller (108) configured to:

receive pressure data from the at least one pressure sensor (106, 116);

control the primary blower (64) to pump inspiration gas into the inspiration tube (26) at a pressure determined from, at least in part, the pressure data from the at least one pressure sensor (106, 116);

detect a failure of the at least one pressure sensor (106, 116); and in response to the detected failure of the at least one pressure sensor (106, 116), control the primary blower (64) to operate at a selected impeller rotational speed selected based on a desired inspiration gas pressure.

51. The ventilator according to claim 50, wherein the controller (108) is further configured to access electronic memory to read information correlating inspiration gas pressure to impeller rotational speed.

* * * * *